United States Patent [19]

Asano et al.

[11] Patent Number: 5,389,849
[45] Date of Patent: Feb. 14, 1995

[54] TACTILITY PROVIDING APPARATUS AND MANIPULATING DEVICE USING THE SAME

[75] Inventors: Takeo Asano, Tokyo; Hisashi Nishimura, Hanno; Nobutoshi Sekiguchi, Hidaka; Hideo Adachi, Iruma, all of Japan

[73] Assignee: Olympus Optical Co., Ltd., Tokyo, Japan

[21] Appl. No.: 179,427

[22] Filed: Jan. 10, 1994

[30] Foreign Application Priority Data

Jan. 20, 1993 [JP] Japan .................................. 5-007196
Mar. 17, 1993 [JP] Japan .................................. 5-057480

[51] Int. Cl.6 ............................................ H01L 41/08
[52] U.S. Cl. ................................... 310/323; 310/328;
340/407.2; 434/114; 901/2; 901/10; 901/23
[58] Field of Search .................... 310/311, 316–319,
310/321–323, 334, 336, 338, 339; 340/407;
434/114; 901/2, 9, 10, 14, 23, 33, 46, 50

[56] References Cited

U.S. PATENT DOCUMENTS

| | | |
|---|---|---|
| 2,475,641 | 7/1949 | Rosenburg ..................... 310/317 X |
| 3,229,387 | 1/1966 | Linvill ........................... 310/316 X |
| 4,546,658 | 10/1985 | Rocha et al. ..................... 310/338 X |
| 4,562,374 | 12/1985 | Sashida ............................. 310/323 |
| 4,634,917 | 1/1987 | Dvorsky et al. ................ 310/323 X |
| 4,712,037 | 12/1987 | Verbeek et al. .................... 310/323 |
| 4,727,278 | 2/1988 | Staufenberg, Jr. et al. ......... 310/328 |
| 4,787,262 | 11/1988 | Kozawa et al. ................ 310/328 X |
| 4,868,447 | 9/1989 | Lee et al. ............................ 310/328 |
| 4,983,875 | 6/1991 | Masaki et al. ....................... 310/323 |
| 5,099,167 | 3/1992 | Kimura et al. ...................... 310/323 |
| 5,258,694 | 11/1993 | Ohnishi et al. ................ 310/323 X |

OTHER PUBLICATIONS

Measurement and Control, "Micromanipulation of Cells", vol. 23, No. 9, pp. 32–38.
Tate and Sakaki, "Impedance Control Type Master/Slave System-Basic Principle and Application to Transmission Delay", Mechanical Technology Research Report, vol. 46, (1992), No. 2, pp. 170–182.

Primary Examiner—Mark O. Budd
Attorney, Agent, or Firm—Frishauf, Holtz, Goodman & Woodward

[57] ABSTRACT

A detecting portion outputs a contact state signal in accordance with a contact state with respect to an object to be manipulated. The contact state signal represents at least one of information of a sense of sliding of the detection portion with respect to the object and surface information such as surface roughness of the object. A signal processing section converts the contact state signal from the detecting portion into tactility information corresponding to at least one of the information of the sense of sliding and the surface information. A tactility providing portion is excited in accordance with the tactility information from the signal processing section to generate at least one of a traveling wave corresponding to the information of the sense of sliding and a standing wave corresponding to the surface information. A transmission portion transmits at least one of the traveling wave and the standing wave generated by the tactility providing portion to a finger of an operator.

20 Claims, 21 Drawing Sheets

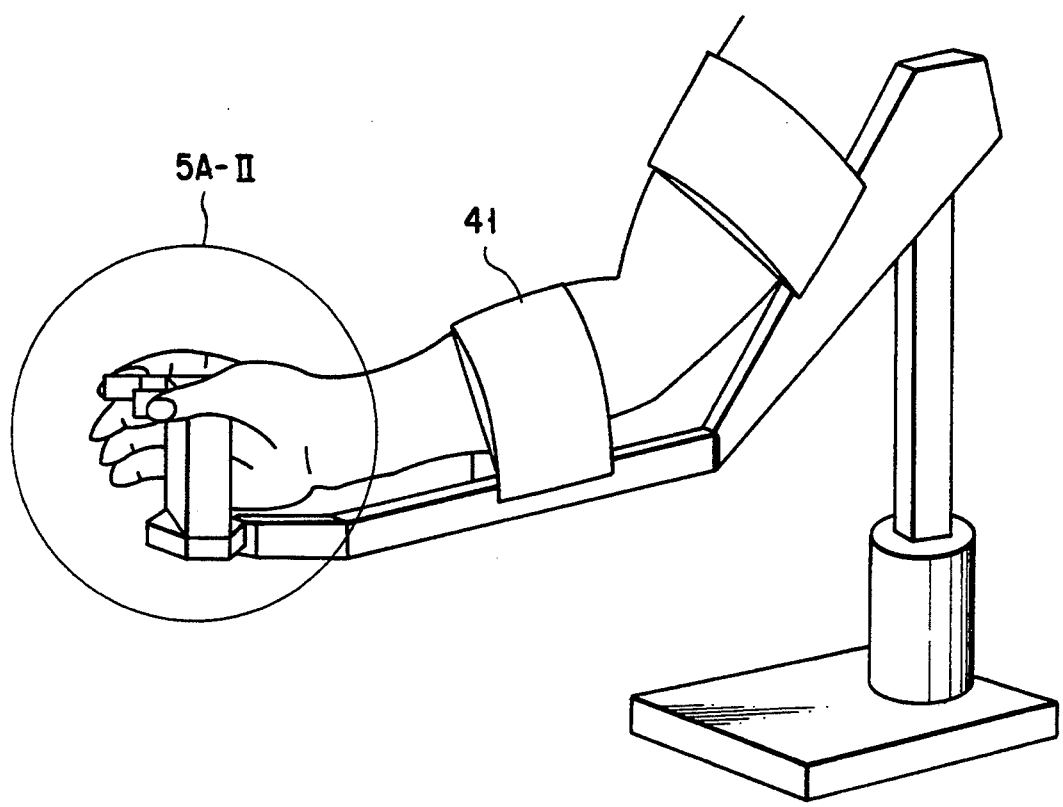
FIG. 5A-I
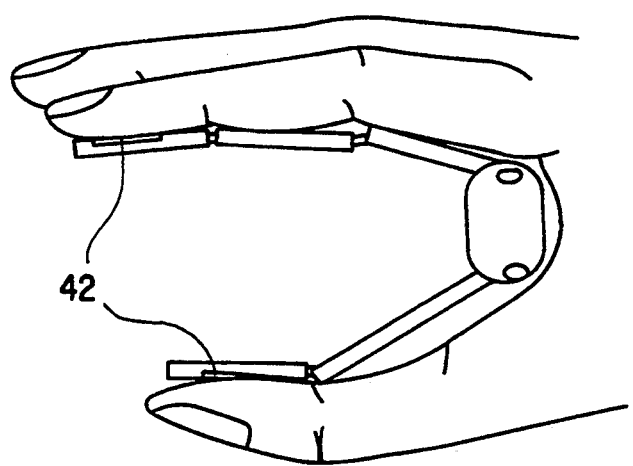
FIG. 5A-II

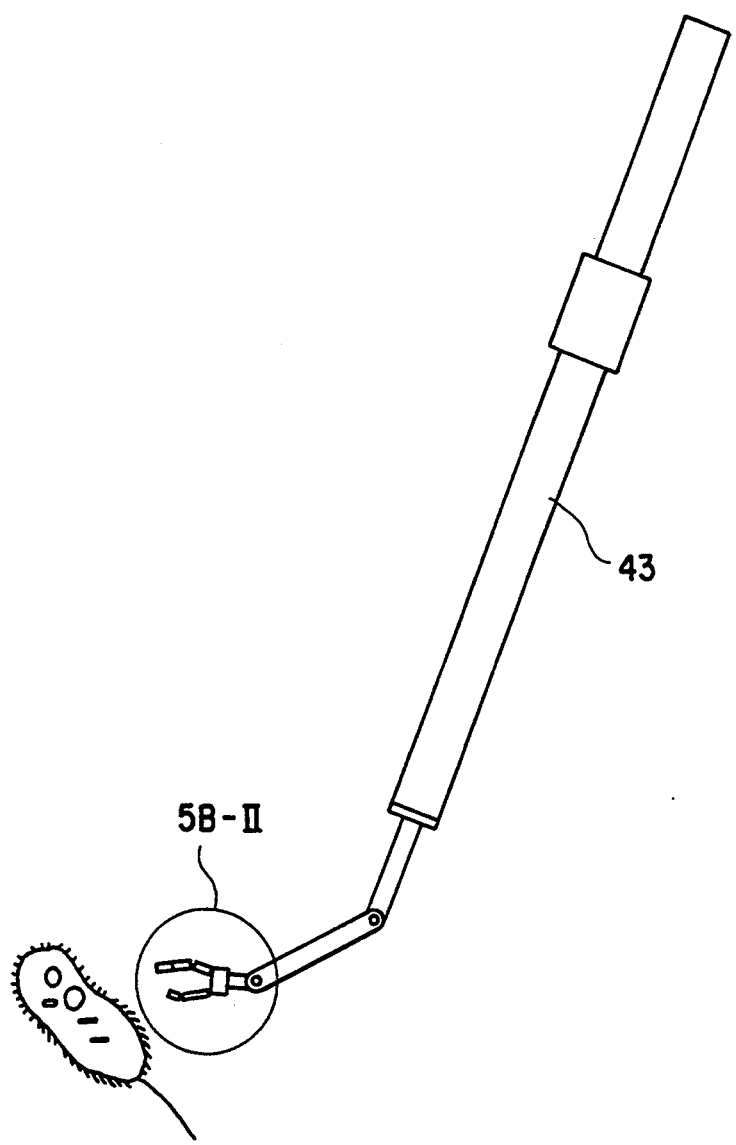
FIG. 5B-I
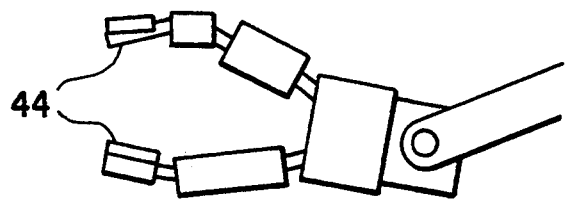
FIG. 5B-II

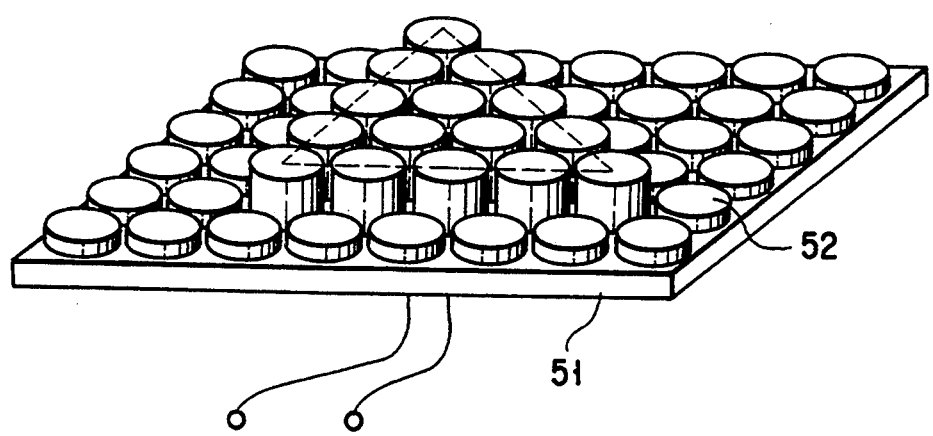
F I G. 8
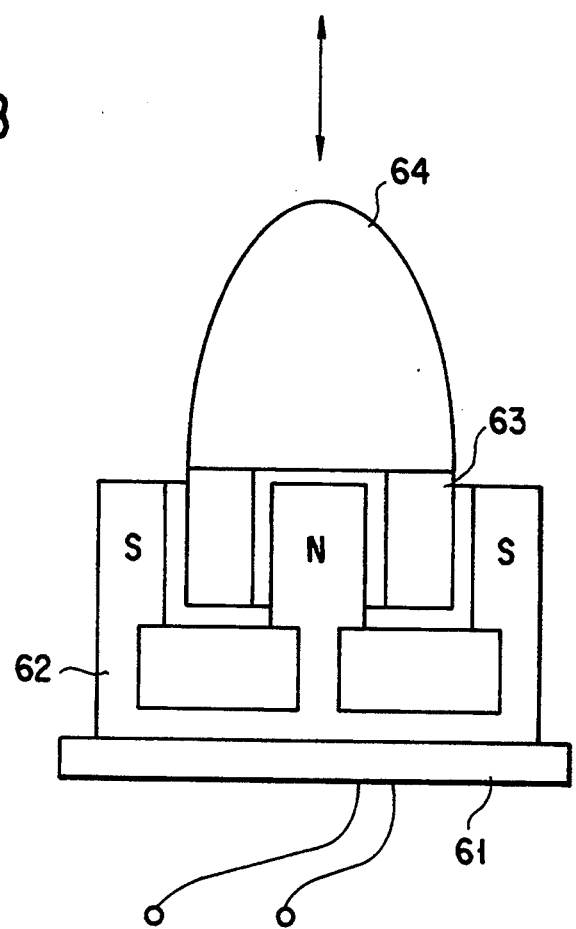
F I G. 9
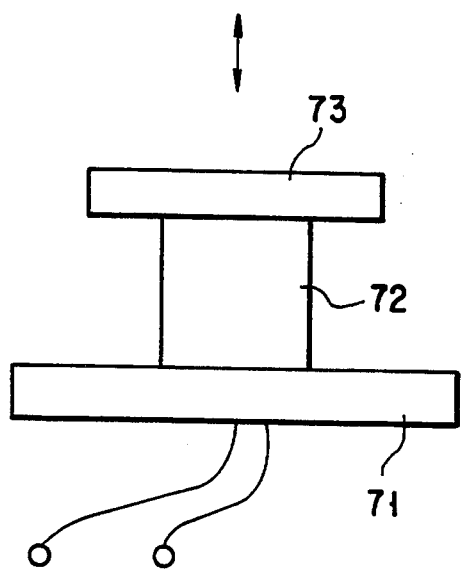
F I G. 10

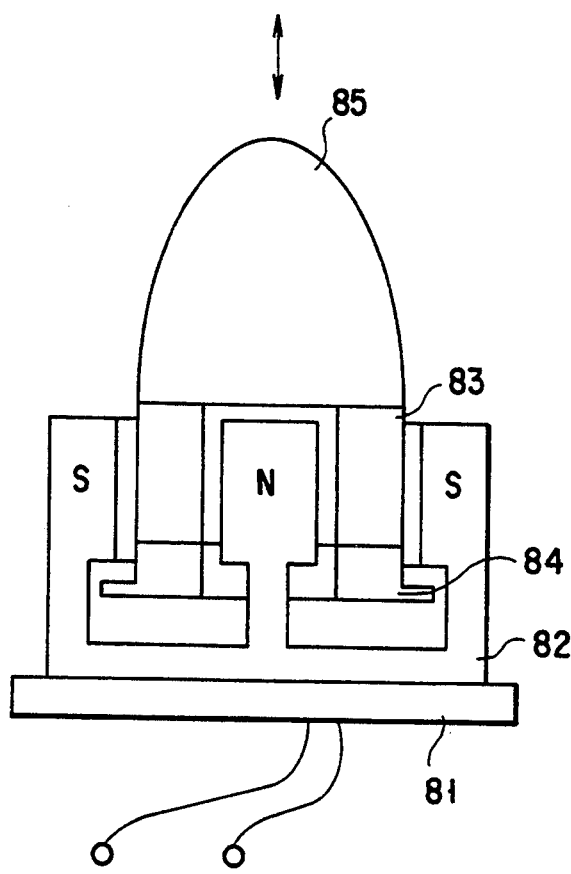
F I G. 11
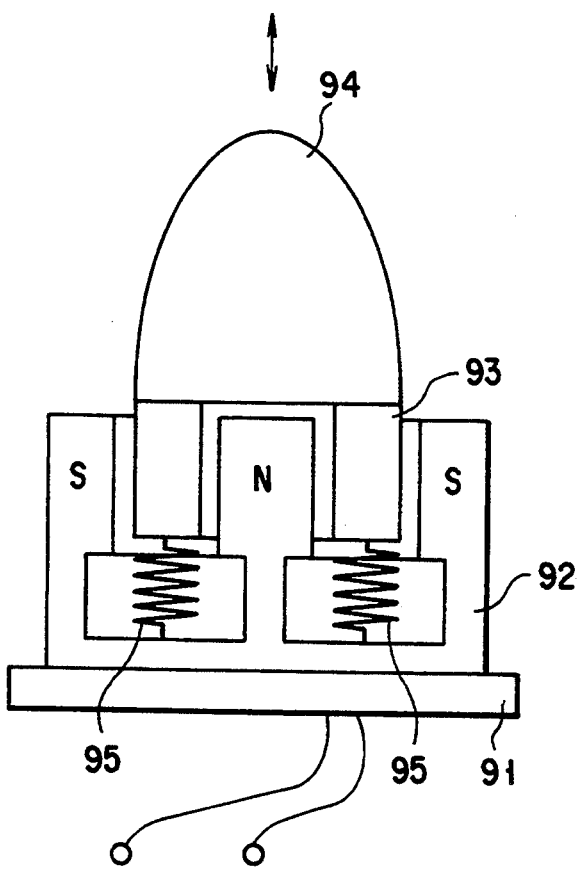
F I G. 12

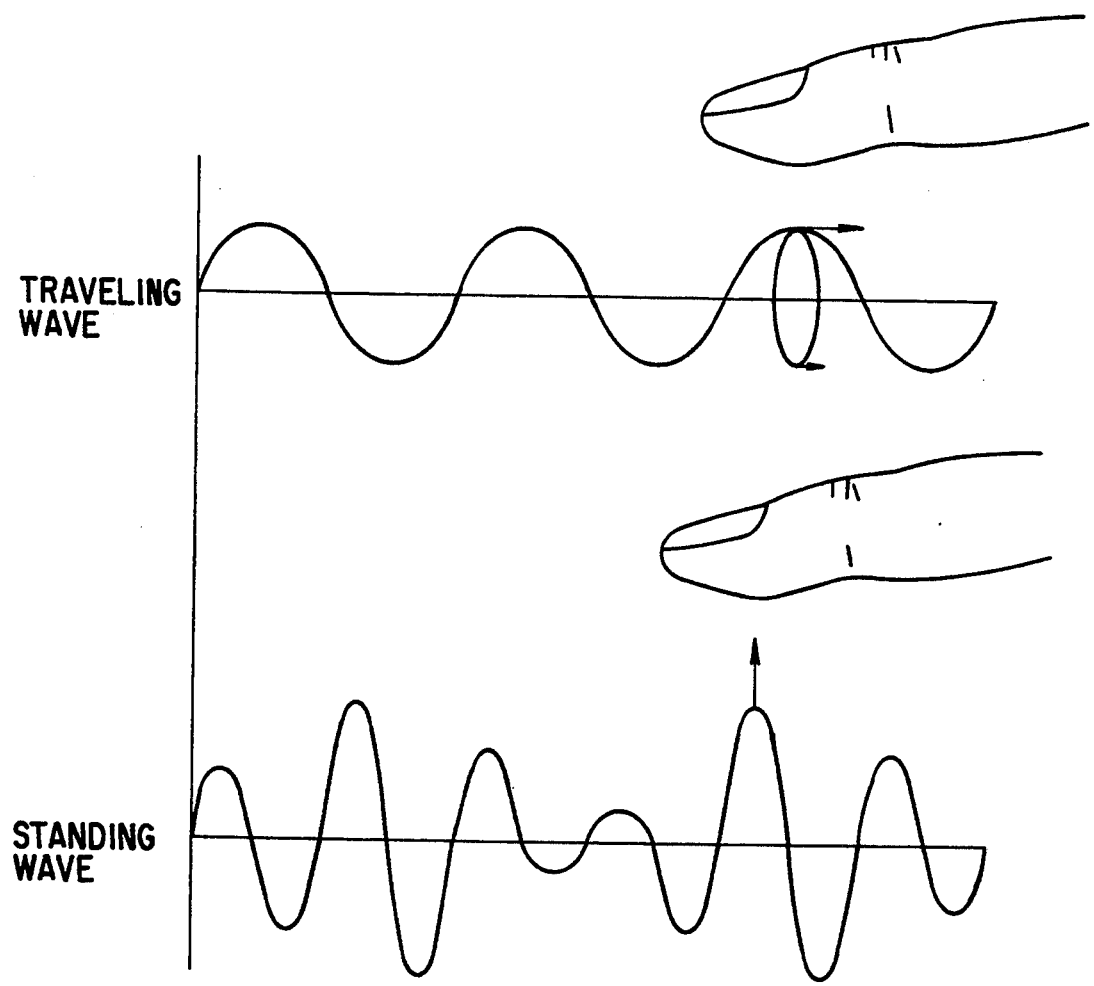
F I G. 13

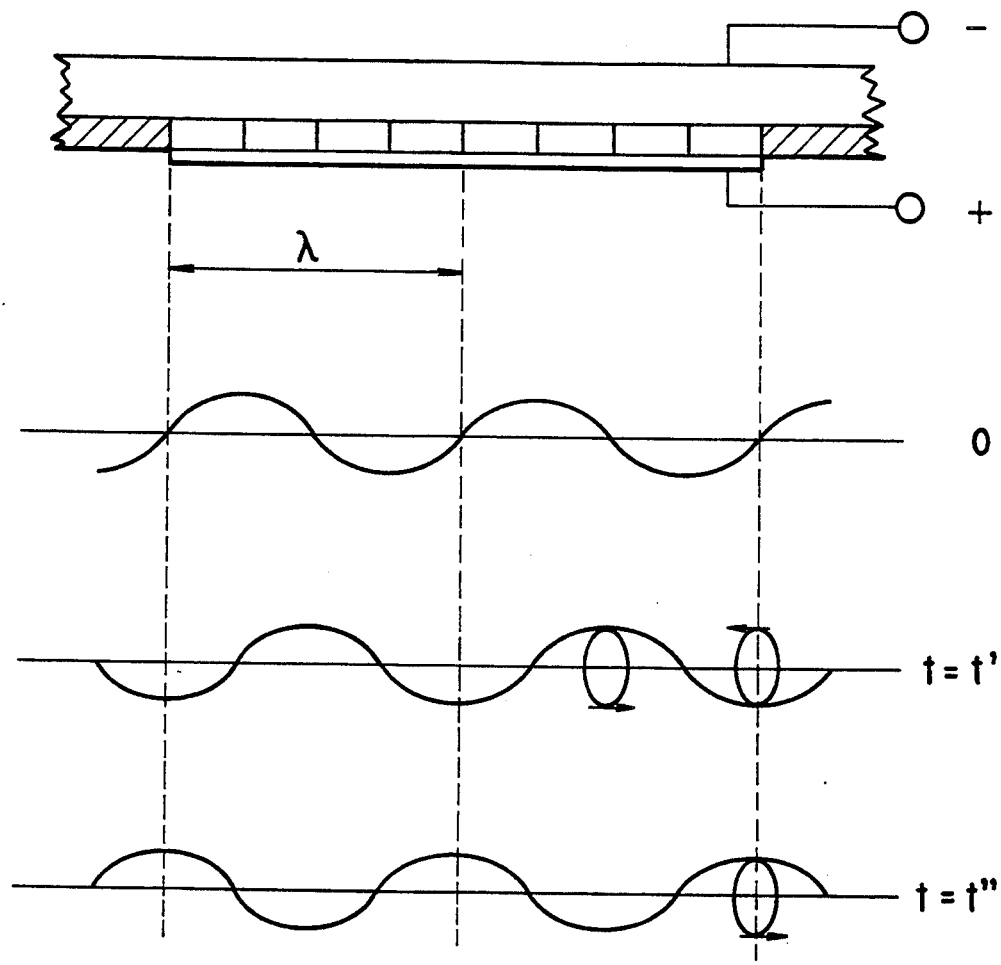
F I G. 17
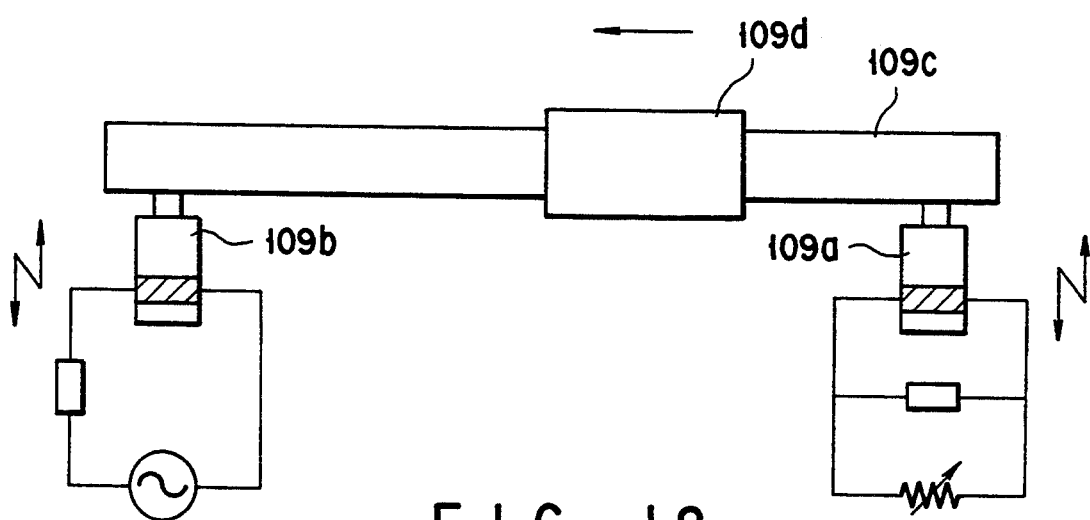
F I G. 18

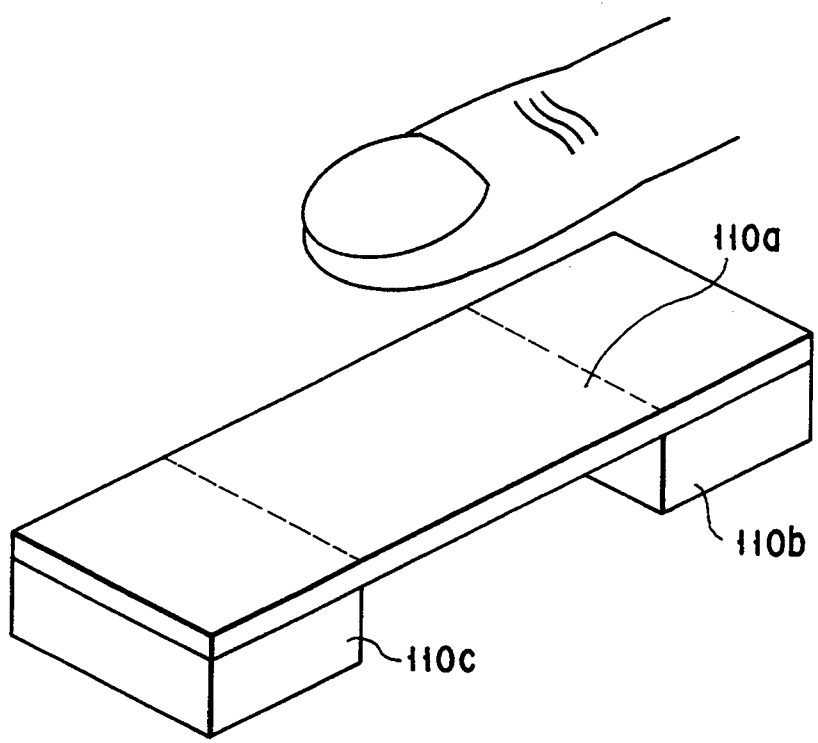
F I G. 19
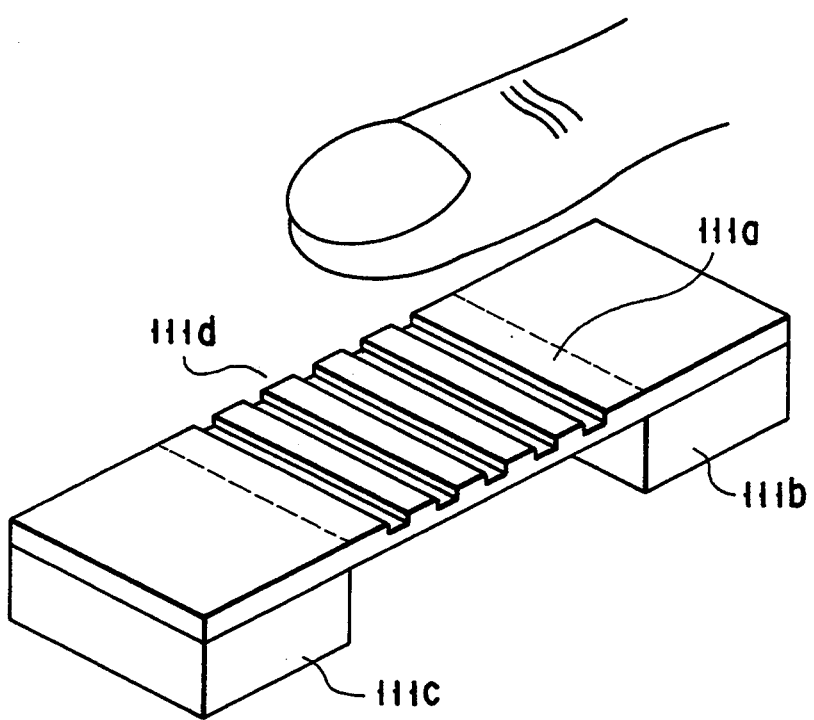
F I G. 20

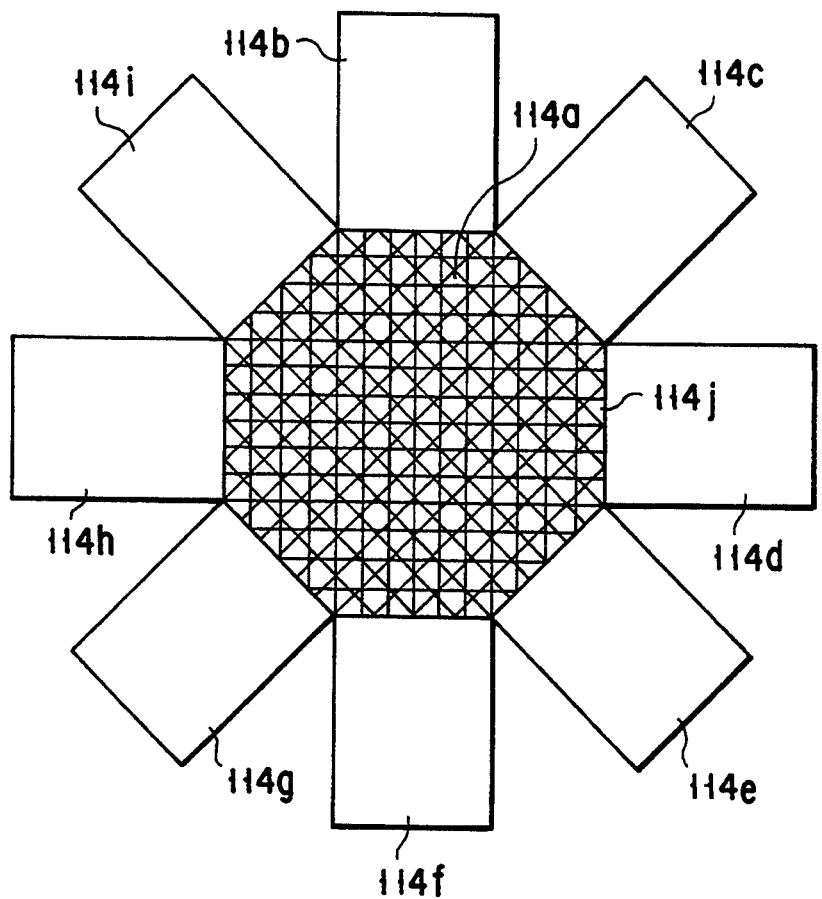
F I G. 23
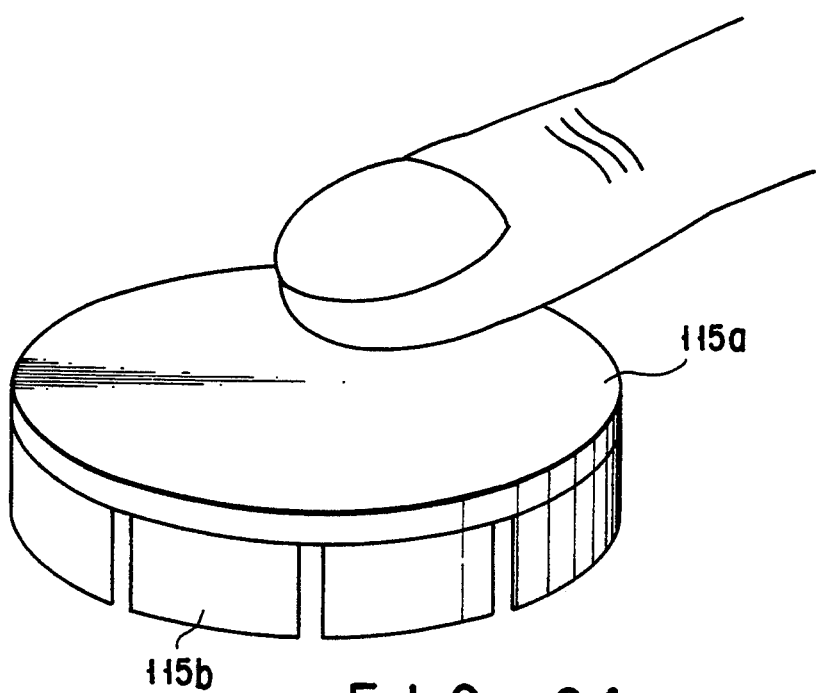
F I G. 24

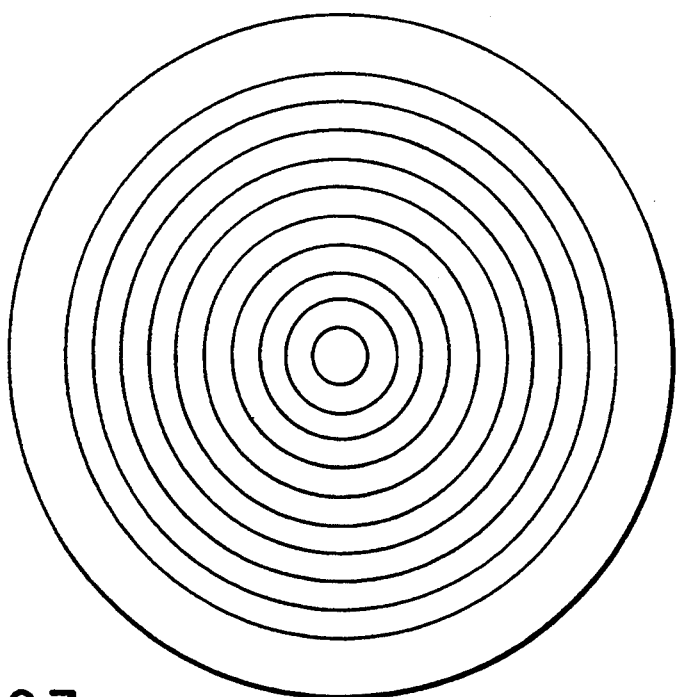
F I G. 27
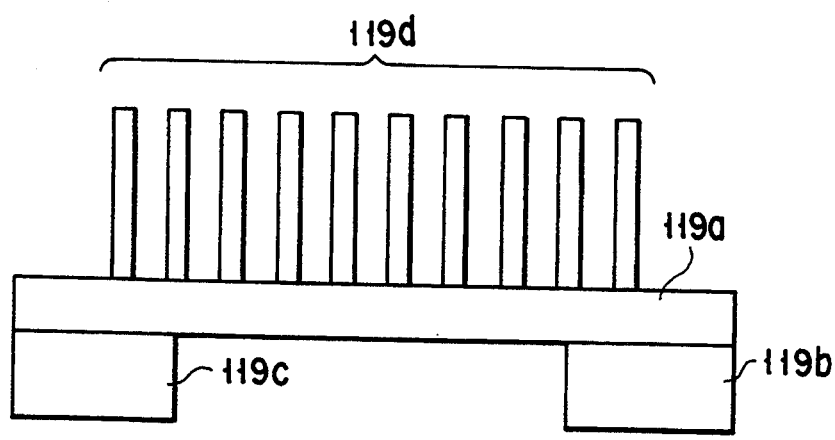
F I G. 28
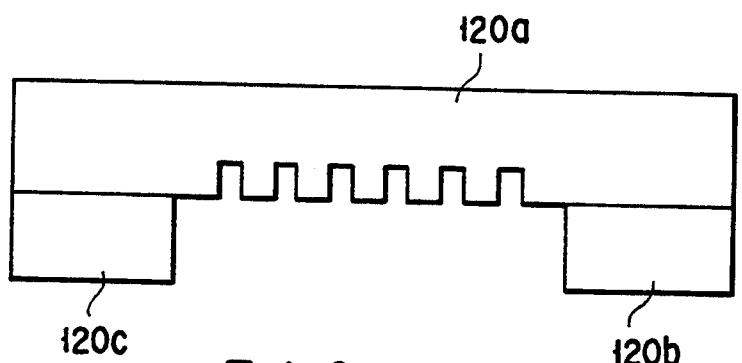
F I G. 29

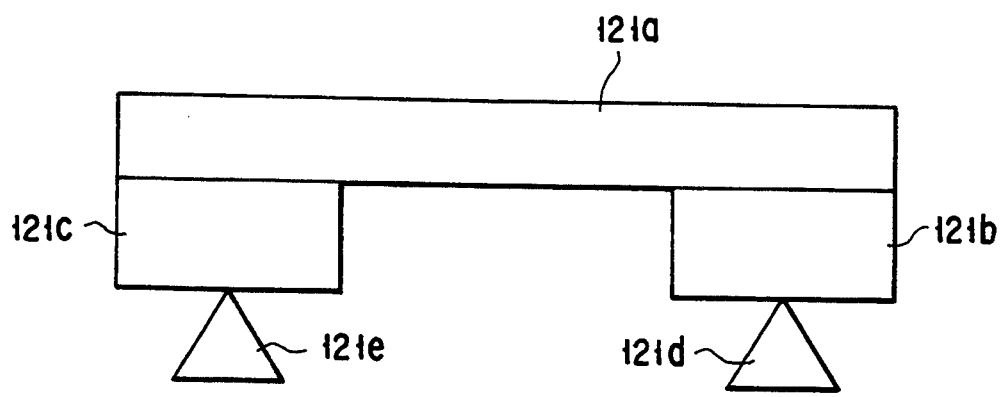
F I G. 30
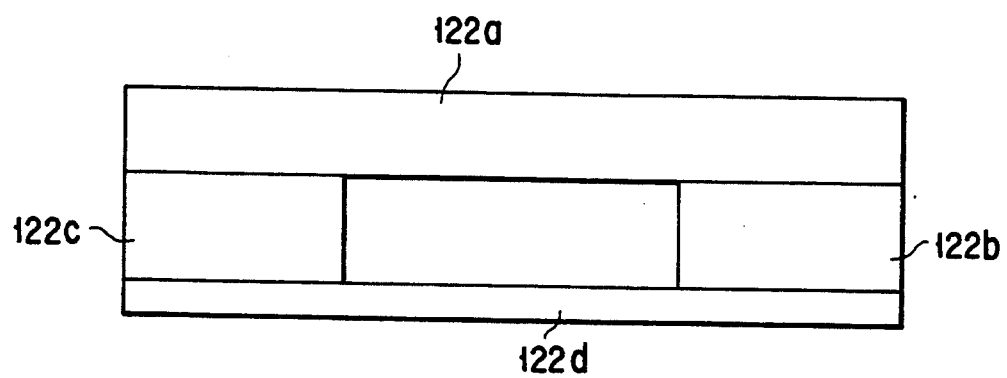
F I G. 31
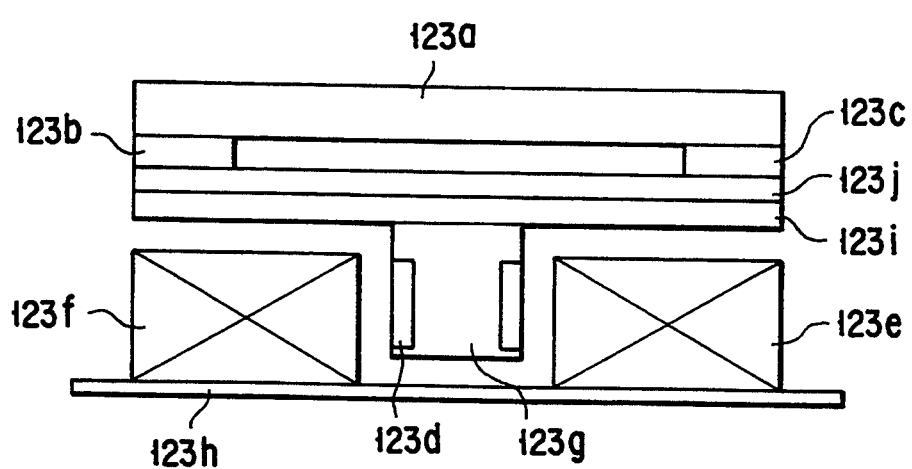
F I G. 32

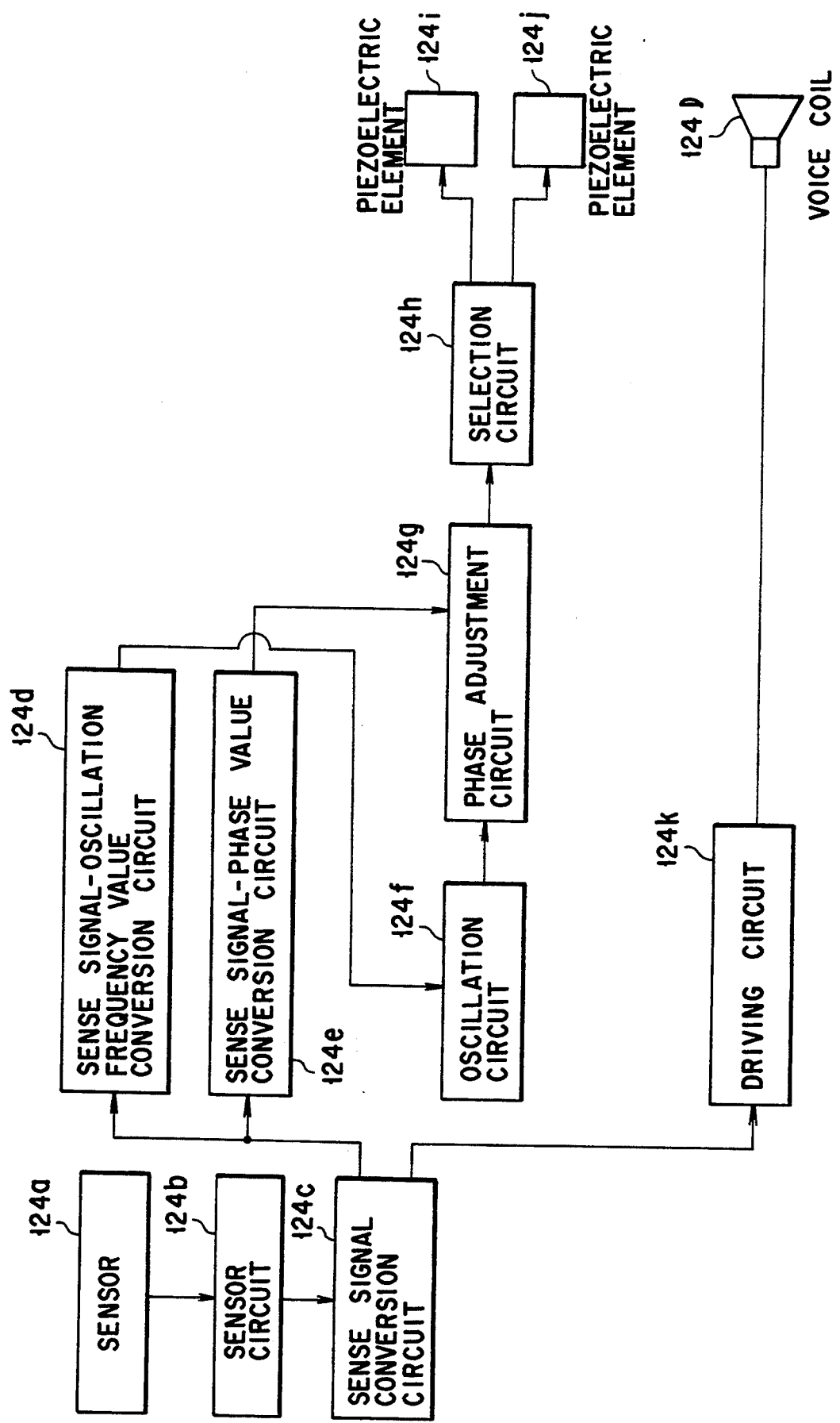
F I G. 33

TACTILITY PROVIDING APPARATUS AND MANIPULATING DEVICE USING THE SAME

BACKGROUND OF THE INVENTION

1. Field of the Invention

The present invention relates to a tactility providing apparatus and a manipulating device using the same and, more particularly, to a tactility providing apparatus for providing tactility information about an object for a tactile Organ of an operator when the object cannot be directly touched, and a manipulating device for performing an operation by transmitting tactility information about an object to the tactile organ of an operator using the tactility providing apparatus when the object cannot be directly touched.

2. Description of the Related Art

A manipulating device is designed to manipulate a microscopic object which cannot be directly touched by an operator or perform an operation in an extremely severe environment. This device is roughly constituted by two portions, i.e., a manipulating portion manipulated by the operator, and an operating portion, e.g., a manipulator, for directly performing an operation with respect to an object. The device allows the operator to indirectly manipulate the object. The following devices are available as such conventional manipulating devices.

FIGS. 34A and 34B show a conventional micromanipulator arranged for a microscope. FIG. 34A shows the overall arrangement. FIG. 34B is an enlarged view of part of the arrangement.

This enlarged view schematically shows a state wherein a microscopic cell such as a fertilized egg is fixed by suction with a pipet, and a reagent is injected into the cell with a needle, or a gene having different genetic information is injected in the cell (see Shikano, "Micromanipulation of Cells", Measurement and Control, Vol. 23, No. 9, pp. 32–38).

A piper $101c$ and a needle $101d$ are operably attached to the microscope. The piper $101c$ serves to fix a cell $101b$, as an object, on a microscope main body $101a$. The needle $101d$ is used to perform an operation with respect to the object.

Joysticks $101e$ and $101f$ for manipulating the pipet $101c$ and the needle $101d$ with the hands of an operator are mounted on the microscope main body $101a$.

The operator performs an operation such as holding, incision, or injection by manipulating the piper $101c$ and the needle $101d$ with the joysticks $101e$ and $101f$ while observing the cell $101b$ through the microscope.

The above-mentioned operation is an indispensable support technique as a technique of manipulating cells, biopolymers, and the like in the recent study of biotechnology.

FIG. 35 shows a manipulator system for a conventional robot. This system is constituted by a slave arm $102c$, a master arm $102f$, fixing members $102g$, and a control system $102h$ (see Tate and Sakaki, "Impedance Control Type Master/Slave System—Basic Principle and Application to Transmission Delay", Mechanical Technology Research Center Report, Vol. 46 (1992), No. 2, pp. 170–182). The slave arm $102c$ has a plurality of joints $102a$ with sensors, and a treatment section $102b$. The master arm $102f$ has a plurality of joints $102d$ with sensors, and a treatment section $102e$ in correspondence with the arrangement of the slave arm $102c$. The fixing members $102g$ serve to fix an arm of an operator to the master arm $102f$ so as to match the degree of freedom of movement of the master arm $102f$ to that of the arm of the operator. The control system $102h$ includes a signal processing circuit for matching the operation of the master arm $102f$ to that of the slave arm $102c$.

When the operator fixes his/her arm to the master arm $102f$ and arbitrarily manipulates it, the operation state controls sensor information to drive the corresponding slave arm $102c$.

The operation of the operator is then reproduced by the slave arm $102c$ through the master arm $102f$. The operator receives an external force, received by the slave arm $102c$, as a direct force through the master arm $102f$.

Various types of manipulator systems have been proposed as well as manipulator systems for robots such as the one described above. Bilateral control methods, impedance control methods, and the like have been developed as methods of improving the operability of robots.

FIGS. 36A and 36B show a forceps as a medical instrument. FIG. 36A shows the overall arrangement. FIG. 36B is an enlarged view of a distal end portion of the forceps.

A forceps 721 is constituted by an insertion portion 722 to be inserted into a body cavity via the trachea or the like of a patient, a forceps portion 723 arranged on the distal end of the insertion portion 722, and a manipulating portion 724 arranged on the proximal end portion of the insertion portion 722.

The forceps portion 723 has a pair of pivotally supported forceps members $726a$ and $726b$. The manipulating portion 724 is constituted by a stationary manipulating handle $727a$ fixed to the proximal end portion of the insertion portion and a movable manipulating handle $727b$ pivotally attached to the proximal end portion. These handles $727a$ and $727b$ serve to open/close the forceps members $726a$ and $726b$.

When the forceps member $726b$ is pivoted, a manipulation shaft (not shown) in the insertion portion slides forward and backward. As a result, the forceps members $726a$ and $726b$ are opened/closed via a link mechanism (not shown).

The following problems are posed in the above-described conventional devices.

In the conventional device shown in FIGS. 34A and 34B, information indicating whether the operating portion is in contact with a sample in a proper state is only obtained as a two-dimensional image observed through the microscope. That is, information in the depth direction is only focus information about the image in spite of the fact that the operation of the operating portion is three-dimensional. For this reason, considerably high skills are required to determine, from such an image, a specific state in which the operating portion is in contact with the object. In practice, therefore, only a skilled person can use such a device.

Furthermore, objects to be studied in, for example, the medical and biotechnological fields are becoming smaller in size, from cells to intracellular substances.

With this trend, observation and manipulating portions for objects are also becoming smaller in size. With this reduction in size, a more sophisticated and accurate manipulation of a manipulator is required.

The robot manipulator shown in FIG. 35 is designed to allow an operator to recognize holding of an object by increasing the sense of resistance upon holding the object. In this case, however, information about the hardness/softness of the object and the like are not expressed in the master arm. That is, the device is not designed to reproduce a state wherein an ordinary person holds the object. Such a level of presentation of a sensation is sufficient for a rough operation such as conveying of an object. However, in a micromanipulator and the like which demand high-precision, minute operations and determinations, the level of presentation of a sensation described above is not sufficient for an improvement in operability by means of presentation of a sense of resistance or accurate recognition of an object to be held.

In manipulating the conventional forceps shown in FIGS. 36A and 36B, a delicate sense of manipulation cannot be obtained owing to its mechanism. For this reason, even a skilled operator is required to perform a very careful, accurate manipulation, e.g., recognizing the lever opening degree of the forceps and a peeled state of a tissue while monitoring an observation image through an abdominal cavity mirror. In practice, therefore, such an operation is limited to only highly skilled operators.

A problem similar to that in the operation of a forceps is assumed in the operation of an endoscope which is inserted into a body cavity to perform observation and medical treatment.

An inserting operation of a currently used endoscope is performed on the basis of only image information observed through the distal end portion and the above-mentioned insertion resistance. It is difficult to insert such an endoscope while predicting a pain felt by a patient when the outer wall of the endoscope is pressed against the inner wall of his/her organ. In addition, with the mechanical arrangement of a currently used endoscope, it is impossible for an operator to obtain information about the correlation between the level of pressure and the pain felt by a patient, i.e., information indicating a specific degree of pressure at which a patient feels a pain, as manipulation information.

As described above, when the above-described conventional manipulating devices are manipulated, operators cannot recognize a specific state in which the operating portion is in contact with a tissue, or cannot obtain information indicating a force with which an object is held. That is, the conventional devices cannot allow operators to recognize a contact or held state or obtain various types of contact information such as the surface roughness and surface temperature of an object.

In the conventional devices, tactility information and held state information about an object and various types of tactility information such as the surface roughness and surface temperature of an object are not fed back to operators. For this reason, a minute, accurate manipulation based on the tactility of a human being cannot be performed.

SUMMARY OF THE INVENTION

It is, therefore, an object of the present invention to provide a new and improved tactility providing apparatus in which surface information including a sense of sliding and surface roughness is transmitted to an operator to allow the operator to manipulate an object with an optimal manipulating force or perform proper determination, thereby eliminating a sense of detachment with respect to a manipulation, which poses a problem at present, improving the function of a device, and allowing a more accurate manipulation with higher operability.

In addition, it is another object of the present invention to provide a manipulating device using a tactility providing apparatus, which transmits a sense of manipulation, as tactility, to an operator to make him/her to feel as if he/she were actually manipulating an object with his/her own hand, to eliminate a sense of detachment with respect to a manipulation, which poses a problem at present, thereby improving the function of the device, and allowing a more accurate manipulation with higher operability.

According to an aspect of the present invention, there is provided a tactility providing apparatus comprising: detection means for outputting a contact state signal in accordance with a contact state with respect to an object to be manipulated, the contact state signal representing at least one of information of a sense of sliding of the detection means with respect to the object and surface information such as surface roughness of the object; signal processing means for converting the contact state signal from the detection means into tactility information corresponding to at least one of the information of the sense of sliding and the surface information; tactility providing means which is excited in accordance with the tactility information from the signal processing means to generate at least one of a traveling wave corresponding to the information of the sense of sliding and a standing wave corresponding to the surface information; and transmission means for transmitting at least one of the traveling wave and the standing wave generated by the tactility providing means to a finger of an operator, wherein while the finger of the operator is in a non-contact state with respect to the object, the information of the sense of sliding with respect to the object is provided to the finger, through the traveling wave transmitted from the transmission means, in accordance with the contact state signal from the detection means, and the surface information about the object is also provided to the finger through the standing wave.

According to another aspect of the present invention, there is provided a manipulation device comprising: an operating portion, having detection means at a predetermined position, for directly manipulating an object, the detection means detecting a contact state with respect to the object and outputting a contact state signal; a manipulating portion having tactility transmission means at a predetermined position, the tactility transmission means transmitting tactility information to an operator in accordance with the signal, the manipulating portion being manipulated by the operator; and a control section, having signal processing means for converting/outputting tactility information about the object on the basis of the contact state signal based on the object and output from the detection means of the operating means, for controlling the tactility transmission means in accordance with the processed signal and controlling the operating portion in accordance with movement of the manipulating portion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 5A-I, 5A-II, 5B-I and 5B-II are views showing an application example in which the manipulating device according to the first embodiment of the present invention is applied to a master/slave system;

FIG. 8 is a perspective view showing an example of expression performed by the tactility transmission member in FIG. 6;

FIG. 9 is a sectional view showing an application example of the driving portion of the tactility transmission member in FIG. 6;

FIG. 10 is a sectional view showing another application example of the driving portion of the tactility transmission member in FIG. 6;

FIG. 11 is a sectional view showing still another application example of the driving portion of the tactility transmission member in FIG. 6;

FIG. 12 is a sectional view showing an application example of a detection member in FIG. 5B;

FIG. 13 is a chart for explaining the propagation states of a traveling wave and a standing wave used for a tactility providing apparatus according to the second embodiment of the present invention;

FIG. 17 is a chart showing the propagation state of a traveling wave to explain the principle of the tactility providing apparatus of the present invention;

FIG. 18 is a view showing the arrangement of a general ultrasonic linear motor to explain the principle of the tactility providing apparatus of the present invention;

FIG. 19 is a perspective view showing the first application example based on the second embodiment of the present invention;

FIG. 20 is a perspective view showing the second application example based on the second embodiment of the present invention;

FIG. 23 is a perspective view showing the fifth application example based on the second embodiment of the present invention;

FIG. 24 is a perspective view showing the sixth application example based on the second embodiment of the present invention;

FIG. 27 is a plan view showing the eighth application example based on the second embodiment of the present invention;

FIG. 28 is a sectional view showing the ninth application example based on the second embodiment of the present invention;

FIG. 29 is a sectional view showing the tenth application example based on the second embodiment of the present invention;

FIG. 30 is a sectional view showing the eleventh application example based on the second embodiment of the present invention;

FIG. 31 is a sectional view showing the twelfth application example based on the second embodiment of the present invention;

FIG. 32 is a sectional view showing the thirteenth application example based on the second embodiment of the present invention;

FIG. 33 is a block diagram showing a typical circuit arrangement used for the second embodiment of the present invention;

DETAILED DESCRIPTION OF THE PREFERRED EMBODIMENTS

Figure 1:
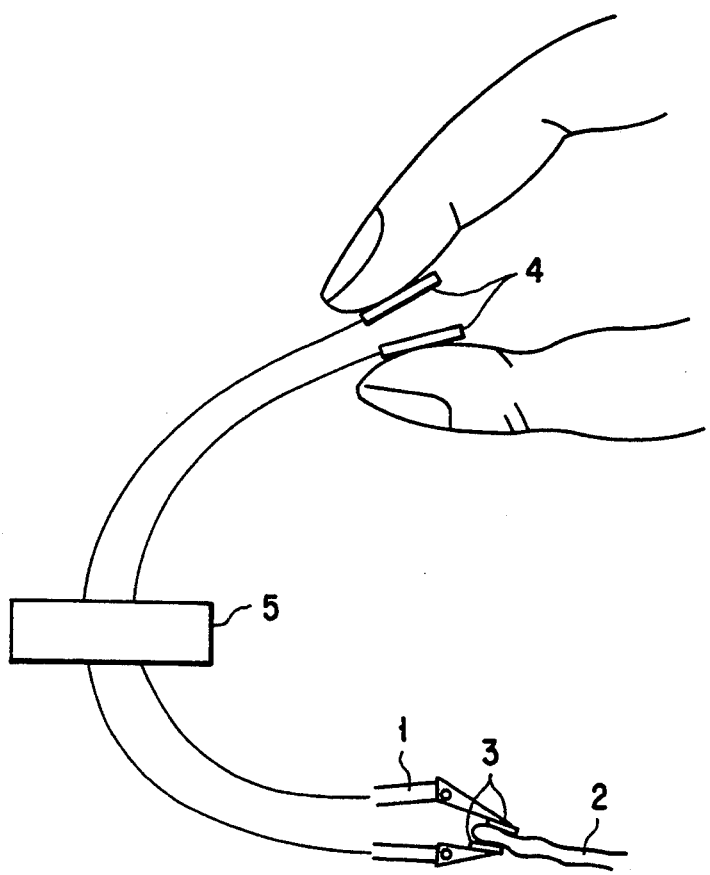
FIG. 1 is a schematic view of the first embodiment of the present invention.

Reference will now be made in detail to the presently preferred embodiments of the invention as illustrated in the accompanying drawings, in which like reference characters designate like or corresponding parts throughout the several drawings. Embodiments of the present invention will be described in detail below. Note that in the following description of each embodiment, tactility information associated with the hardness of an object will be discussed.

FIG. 1 is a schematic view of the first embodiment of the present invention.

A transducer 3 as an example of a detecting portion designed to electro-mechanically generate a signal is attached to each of the distal end portions, of a slave manipulator 1 for holding an object 2, which are designed to hold the object 2. A tactility transmission portion 4 for transmitting a signal from the transducer 3, as a contact pressure, to a finger of an operator is connected to the transducer 3 via a signal processing section 5.

In the use of an apparatus having the above-described arrangement, when the operator manipulates a manipulating means (not shown), the object 2 is held by the slave manipulator 1. At this time, the transducer 3 attached to the distal end portion of the slave manipulator 1 is brought into contact with the object 2. The transducer 3, serving as a sensing portion of the slave manipulator 1, is designed to electro-mechanically generate a signal in accordance with a stress applied to an object by the slave manipulator 1. Therefore, when the manipulating means is operated, a tactility signal is generated. This tactility signal is converted into a driving signal for the tactility transmission portion 4 by the signal processing section 5. When the signal is sent to the tactility transmission portion 4, a pressure at which the object 2 is held is transmitted to a finger of the operator. This pressure is given by vibrating the tactility transmission portion 4 at a frequency corresponding to an input from the transducer 3 which exceeds the time response limit of the tactility of a human being. The time response limit associated with the tactility of a human being is assumed to be about 200 Hz. In addition, a human being feels rigidity, e.g., hardness and softness, with respect to an object which vibrates at a frequency exceeding the time response limit.

Figure 2:
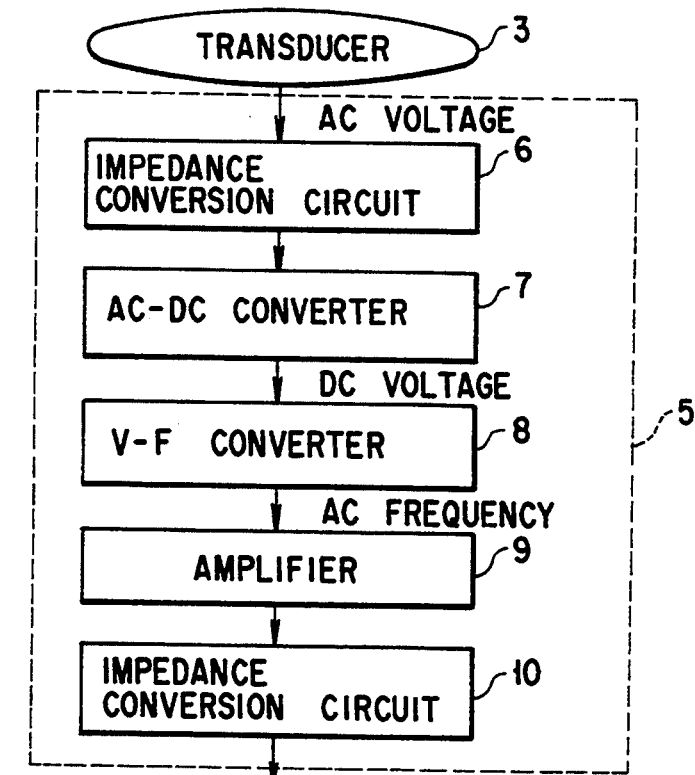
FIG. 2 is a flow chart showing the flow of processing in a signal processing section in FIG. 1.

FIG. 2 shows the flow of processing performed by the signal processing section 5. The arrangement for this signal processing changes depending on the type of output signal from a detecting portion arranged on an operating portion.

For example, FIG. 2 shows a case wherein a signal is output as an AC voltage. In this arrangement, an impedance converter 6 performs impedance matching with respect to a signal electro-mechanically generated by the transducer 3 in accordance with the detected contact state with respect to an object. The resultant signal is input to a V-F converter 8 via an AC-DC converter 7 and is output via an amplifier 9 and an impedance converter 10, thereby generating a signal for driving the tactility transmission portion 4.

In this processing, in accordance with the signal, the tactility transmission portion 4 which is in contact with the respective fingers provides a sense of pressure to the fingers to make the operator feel as if he/she were actually touching the object. In addition, a repulsion against a pressing operation is transmitted as a change in sense of resistance. As a result, the operator can recognize/determine the transmitted results through the fingers to sense the contact state with respect to the object and be free from a sense of detachment with respect to an operation, thereby improving the function, accuracy, and operability of the apparatus.

Figure 3:
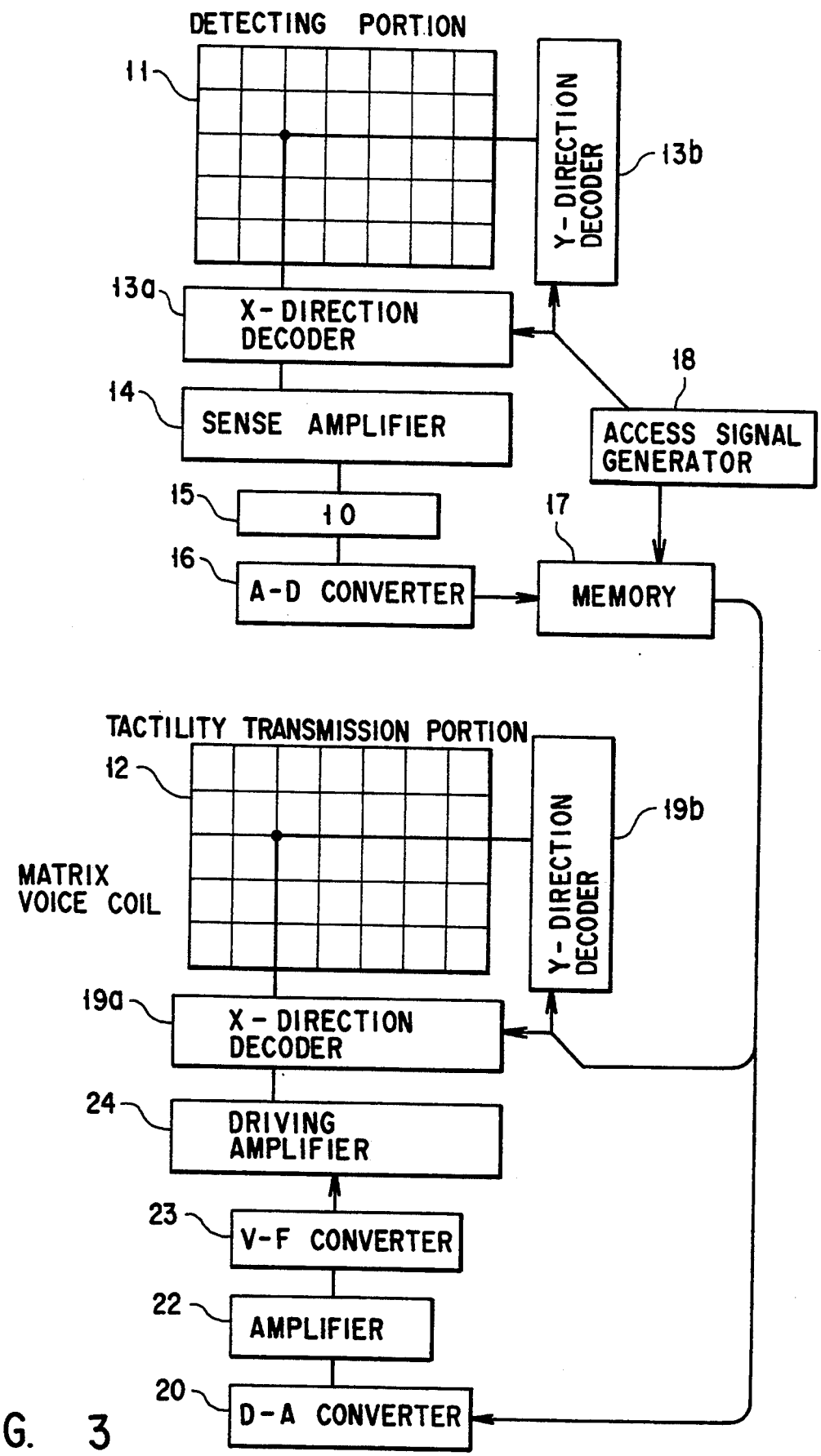
FIG. 3 is a block diagram schematically showing signal processing in a manipulating device according to the first embodiment of the present invention.

FIG. 3 is a block diagram schematically showing signal processing to explain the flows of signals in the overall manipulating device.

In this case, as a detecting portion 11, an electrostatic capacitance type sensor using a change in electrostatic capacity is used, and as a tactility transmission portion 12, a transmission portion constituted by a matrix of voice coils using vibrations generated by an AC power supply is used.

X- and Y-direction decoders 13a and 13b are connected to the detecting portion 11. A sense amplifier 14, an interface 15, and an A-D converter 16 are sequentially connected to the X-direction decoder 13a. In addition, an access signal generator 18 connected to the X- and Y-direction decoders 13a and 13b is connected to a memory 17 which, in turn, is connected to the A-D converter 16.

The memory 17 is connected to X- and Y-direction decoders 19a and 19b, which are connected to the tactility transmission portion 12, and to a D-A converter 20 so that the tactility transmission portion is driven in accordance with data stored in the memory 17. The D-A converter 20 is connected to a driving amplifier 24 connected to a pressure-voltage converter 21, an amplifier 22, a V-F converter 23, and the X-direction decoder 19a.

With this arrangement, when a location to be subjected to detection is designated by an access signal generated by the access signal generator 18, pressure information is obtained from the detecting portion 11 via the decoders 13a and 13b. This pressure information is converted into a digital signal through the sense amplifier 14, the interface 15, and the A-D converter 16 to be stored in the memory 17 together with location data from the access signal generator 18. The tactility transmission portion 12 is driven in accordance with the data stored in the memory 17 in the following manner.

The pressure information converted into the digital signal is restored to a voltage as an analog signal by the D-A converter 20. This voltage is amplified by the amplifier 22 and is converted into a frequency by the V-F converter 23. In this case, by inputting the frequency using the driving amplifier 24, the voice coil at the position designated by the location data stored in the memory 17 is vibrated. In this procedure, the voice coils at positions corresponding to detection results from the respective sensors of the detecting portion 11 are driven, thereby independently controlling the respective voice coils.

An application example to which the first embodiment of the present invention is applied will be described in detail next.

Figure 4A:
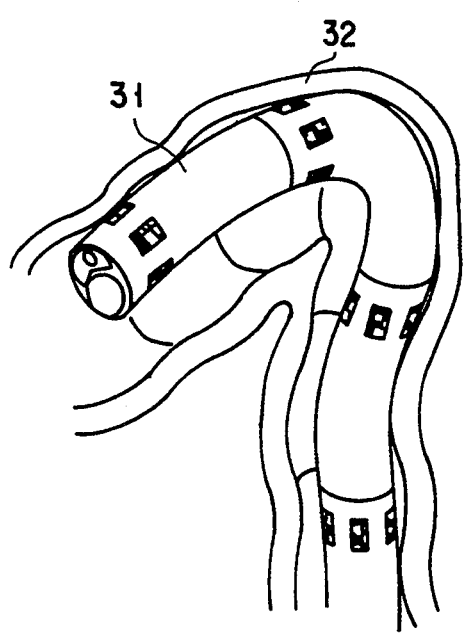
FIGS. 4A and 4B are views showing an application example in which the manipulating device according to the first embodiment of the present invention is applied to an endoscope.
Figure 4B:
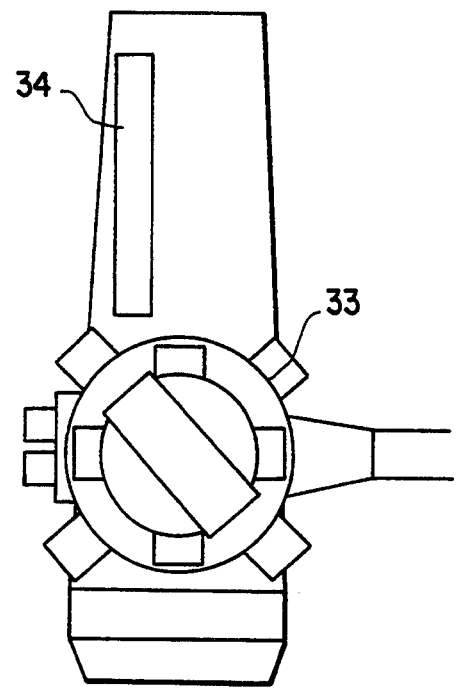

FIGS. 4A and 4B show an application example in which the manipulating device of the present invention is applied to an endoscope. FIG. 4A shows an endoscope insertion portion. FIG. 4B shows an endoscope manipulating portion.

A plurality of tactility sensors 32 as detecting members are attached to the outer surface of an endoscope 31 on circumferences separated by predetermined intervals. A tactility transmission member 34 is arranged in an endoscope manipulating portion 33. Although not shown in FIGS. 4A and 4B, in the tactility transmission member 34, a plurality of driving portions are arranged in a matrix form to be positioned in correspondence with the respective tactility sensors 32, and the tactility sensors 32 as detection means are connected to the tactility transmission member 34 through a signal processing means (not shown), as will be described later.

When the endoscope is inserted into an organ in the manner shown in FIG. 4A, an endoscope body portion is pressed against the side wall of the organ with a high pressure. In such a case, one of the tactility sensors 32 arranged on the body portion of the endoscope 31 which corresponds to the bent portion of the inner wall of the organ detects the pressure and sends the corresponding information to a signal processing means (not shown). The signal representing the contact state, processed by the signal processing means, transmits the pressure information about the endoscope with respect to the inner wall of the organ to the operator through the corresponding portion of the tactility transmission member 34 arranged in the endoscope manipulating portion 33.

Therefore, by applying the present invention to an endoscope, an operator can obtain tactility information and hence can accurately sense a contact pressure acting on an object, thereby greatly improving the operability of the endoscope. That is, in the state shown in FIG. 4A, the operator can adjust the pressure of the endoscope on the inner wall of the organ with a proper force, thereby preventing the patient from suffering the pressure applied on the inner wall of the organ upon forcible insertion of the endoscope.

FIGS. 5A-I to 5B-II show an application example in which the tactility transmission device as the manipulating device according to the first embodiment of the present invention is applied to a master/slave system. FIGS. 5A-I and 5A-II show the master side. FIGS. 5B-I and 5B-II show the slave side.

A master manipulator 41 serves to transmit an operation performed by an operator and has sensors at an arm and joints of fingers of the operator. Tactility transmission members 42 are attached to a portion, of the master manipulator 41, which serves to transmit a holding operation an object. A slave manipulator 43 has sensors mounted on the respective Joints corresponding to the arm and the fingers. Detection members 44 are arranged on holding portions, formed on the distal end of the slave manipulator 43, which correspond to the fingers. The master manipulator 41 and the slave manipulator 43 are connected to each other through a control section (not shown).

The operator fixes his/her arm to the master manipulator 41, and moves the arm to simultaneously move the master manipulator 41. At this time, since the sensors are attached to the arm and the Joints of the fingers of the master manipulator 41, the control section drives actuators arranged for the respective Joints of the slave manipulator 43 upon the operation of the master manipulator 41, thereby reproducing the operation of the operator.

When the holding portions of the master manipulator 41 hold an object, the detection members 44 mounted on the distal end portions of the master manipulator 41 detect the hardness, surface roughness, and the like of the object, and output a contact state signal. The control section controls the tactility transmission members 42 mounted on the holding portions of the master manipulator 41 in accordance with a signal obtained by converting the contact state signal with respect to the object into tactility information.

With this operation, the operator can obtain a sense of manipulating the object with his/her own hand, thus enabling a more accurate operation with higher operability.

Figure 6:
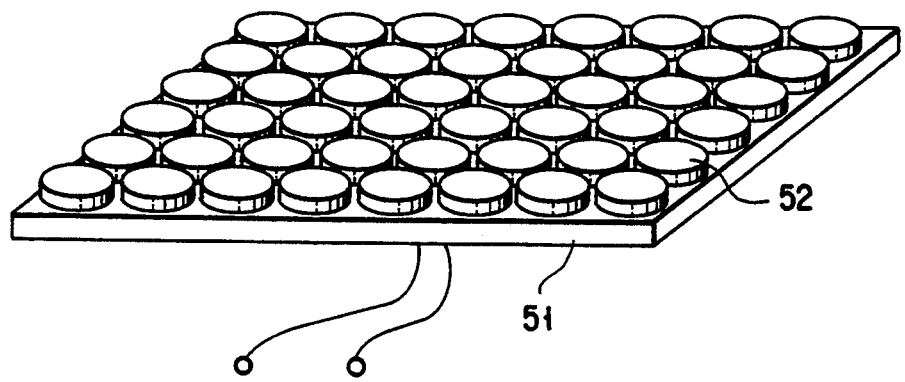
FIG. 6 is a perspective view showing an application example of a tactility transmission member in FIGS. 5A-I and 5B-II.

FIG. 6 shows the details of a tactility transmission member associated with the first embodiment of the present invention and applied to the above-described application example.

In this tactility transmission member, a plurality of driving portions 52 are arranged on a base 51 in a matrix form.

The driving portions 52 are independently controlled, and properties, e.g., hardness and softness, of an object are expressed by various pressures obtained from vibrations generated by the respective driving portions 52.

Figure 7:
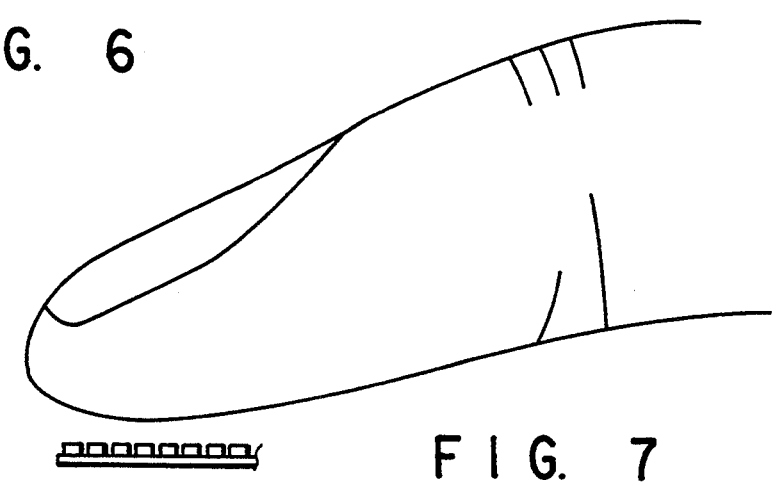
FIG. 7 is a perspective view showing a manipulation of the tactility transmission member in FIG. 6.

For example, this tactility transmission member is used to transmit tactility to a finger tip, as shown in FIG. 7, and has a size of about 10 mm × 15 mm × 3 mm, provided that the member is constituted by a 6 × 8 matrix of driving portions.

FIG. 8 shows a state of the tactility transmission member, in which state the tactility transmission member has actually detected an object and transmits the corresponding information to the operator. Referring to FIG. 8, the triangular shape indicated by the broken lines is transmitted to the operator.

Each driving portion of such a tactility transmission member will be described in detail next.

FIG. 9 shows an application example in which a voice coil is used for a tactility transmission member. This application example is constituted by a circular coil 63 having a tactility transmission portion 64, on its upper portion, between the N and S poles of a circular magnet 62 on a base 61. The central and peripheral portions of the magnet 62 respectively serve as the N and S poles.

Such a voice coil serves as a device for converting an AC current into mechanical vibrations through a magnetic circuit. When the frequency of a current supplied to the coil 63 is set to exceed the tactility response limit, the operator senses the resultant vibrations as a pressure through the skin of a finger. Therefore, a voice coil to which a high-frequency AC current is supplied can be used as a tactility transmission member.

In addition, by coupling a plurality of such voice coils, and independently controlling them, a lateral vibration component can be generated.

FIG. 10 shows a case wherein a PZT is used for a device for giving a stimulus to cutaneous nerves in place of the above-described voice coil.

This device is formed by arranging a PZT 72 on a base 71, and disposing a tactility transmission portion 73 on the PZT 72. A great deal of attention has been paid to a PZT as a microactuator because of its size. It is expected that the device using a PZT can be reduced in size as compared with the one using a voice coil. Assume that the PZT 72 has a size of about 1 mm (diameter) × 2 mm (length).

The PZT 72 deforms in accordance with an applied potential. The PZT 72 is arranged to deform in the vertical direction so as to displace the tactility transmission portion 73 in the vertical direction, thereby giving a stimulus to the skin of a finger. In addition, as in the case of the voice coil described above, when the potential of the PZT 72 is changed at a high frequency, i.e., a frequency exceeding the time response limit of the tactility of a human being with respect to vibrations so as to generate vibrations, a pressure is transmitted through the tactility transmission portion 73 to be sensed by the operator through his/her skin of a finger. With this operation, tactility information associated with hardness can be transmitted.

FIG. 11 shows a device for proving tactility for the skin of a finger by supplying a DC current to a voice coil.

In this device, a magnet 82, e.g., a permanent magnet or an electromagnet, is disposed on a base 81. A coil 83 is arranged to be surrounded with this magnet 82 and linked with a uniform magnetic field generated by the magnet 82. A stopper 84 for defining a movable range and a tactility transmission portion 85 are integrally formed on the lower and upper portions of the coil 83, respectively.

The stopper 84 is not limited to the above-mentioned position and may be mounted at any position as long as it serves to define the movable range. In addition, the masses of the coil 83, the stopper 84, and the tactility transmission portion 85 are negligibly small as compared with a force generated by the coil 83 when a current is supplied thereto.

When a DC current is supplied to the coil 83, a force proportional to the current is generated by the coil 83 in the vertical direction with the force generated by the coil 83, the tactility transmission portion 85 is moved upward or downward and is stopped at a certain position by the stopper 84. With this operation, the tactility transmission portion can express either a protruding state (upward) or a depressed state (downward). In the protruding state, by changing the magnitude of a current, a pressure can be expressed. If, for example, the current is increased to increase the upward force of the coil 83, the operator senses hardness through the skin of a finger in contact with the tactility transmission portion 85. In contrast to this, if a smaller current is supplied to the coil 83, the upward force decreases, and the operator senses softness through the skin of the finger in contact with the tactility transmission portion 85.

Apparently, in this case, if a plurality of voice coils are used, the directivity of tactility can be expressed.

In addition, the coil described as a movable portion may be fixed, while the magnet may be used as a movable portion. In this case, since the coil to be controlled is directly fixed to the base, the resultant arrangement is advantageous for the present invention wherein it is important to realize miniaturization.

FIG. 12 shows an embodiment in which the above-described voice coil, the application of which to a tactility transmission device has been considered so far, is applied to a detection member as a contact sensor.

A magnet 92 such as a permanent magnet or an electromagnet is disposed on a base 91. A coil 93 is arranged to be surrounded with the magnet 92 and linked with a uniform magnetic field generated by the magnet 92. A tactility sensing portion 94 is integrally formed on the upper portion of the coil 93, whereas coil springs 95, each having one end fixed to the magnet 92, are coupled to the lower portion of the coil 93.

In this case, the coil springs are used as members for generating elastic forces. It is, however, apparent that elastic members such as leaf springs, other than the coil springs, can be used.

The device having this arrangement operates as follows.

In the initial state, the coil 93 and the tactility sensing portion 94 stay at given positions owing to the balance between the force generated by a DC current supplied to the coil 93 in the magnetic field and the elastic forces generated by the coil springs 95. When the detection member collides with a certain object, the tactility sensing portion 94 starts to move. In this case, the tactility sensing portion 94 receives a force based on the difference between the elastic force, which changes when the coil springs 95 contract upon collision with the object, and the force which is generated by the current in the initial state. This force can be expressed as a simple function.

The coil 93 fixed to the tactility sensing portion 94 moves in the same manner as described above. When the coil 93 moves in the uniform magnetic field generated by the magnet 92, a counter electromotive force is generated. It is apparent from the Fleming's rule that the magnitude of this counter electromotive force is proportional to the moving speed of the coil 93. That is, by measuring the counter electromotive force, the speeds of the coil 93 and the tactility sensing portion 94 can be calculated. It is assumed that tactility can be defined by a force applied to an object and a value associated with the position or speed as a function of time upon movement of the object by the force. Therefore, by processing this speed data at certain time intervals, and considering the relationship between the forces which act on the tactility sensing portion 94 and the object, and which can be obtained by calculations, tactility can be measured.

The present invention is not limited to the above-described embodiments.

In the above embodiments, as tactility information, the hardness of an object is assumed. However, for example, various types of information, e.g., the surface roughness (smoothness and a sense of sliding) and the surface temperature (warmness), which can be sensed by touching, can be treated.

When surface temperatures are to be treated, a temperature sensor is used as a detection means together with a transducer. In addition, as a tactility transmission means, a fluid such as a gas or a liquid is used. By controlling the fluid temperature on the basis of information obtained by the temperature sensor, tactility information including temperature information can be transmitted to an operator.

Various changes and modifications can be made within the spirit and scope of the invention.

As described above, according to the first embodiment of the present invention, a detected contact state is converted into tactility information about an object, and the tactility information is output to be fed back to an operator so that the operator can obtain a sense of actually manipulating the object with his/her own hand. This eliminates a sense of detachment with respect to an operation to improve the function of the device, allowing a more accurate operation with higher operability.

The above-described first embodiment relates to a tactility providing apparatus for transmitting a sense of actually manipulating an object, as tactility information, to an operator to improve the function of a manipulating device by eliminating a sense of detachment with respect to an operation, which poses a problem at present, and to provide a more accurate device with higher operability, and its system and, more particularly, to a tactility providing portion and a device structure.

FIG. 11 especially shows the electro-mechanical conversion transducer constituted by the base 81, the coil 83, the magnet 82, the stopper 84, and the tactility transmission portion 85.

In this device, the tactility transmission portion 85 is driven at a frequency exceeding the time response limit of the tactility of a human being by using the voice coil constituted by the coil 83 and the magnet 82 so as to transmit hardness/softness information about an object to a finger tip of an operator, placed on the tactility transmit portion 85. In addition, by changing the amount of a current flowing in the voice coil, the coercive force of the tactility transmit portion 85 is changed to transmit a repulsion from the object upon application of a force which collapses or smashes the object. Thus, the operator can obtain a sense of actually manipulating the object with his/her own hand.

In the tactility providing apparatus of the first embodiment, however, only senses such as the hardness, softness, and a sense of repulsion of an object can be transmitted, and it is difficult, in terms of the arrangement, to transmit surface information about the object, such as a sense of sliding and surface roughness.

Surface information such as a sense of sliding or surface roughness is an important control parameter when a person holds and manipulates objects.

That is, an optimal force applied to an object when a person holds and manipulates the object is determined by feeding back various types of information including a sense of sliding of the object on a finger tip.

Therefore, in order to determine a manipulating force matching a specific object and manipulation thereof, it is very important to transmit a sense of sliding and surface information.

The second embodiment obtained by improving the first embodiment with regard to the above point will be described next.

The process of realizing the second embodiment of the present invention and its background as a principle will be described first.

The first embodiment relates to the tactility providing apparatus capable of transmitting hardness/softness information about an object. That is, a sensation transmitted to an operator is tactility in a direction perpendicular to a finger tip of the operator.

In contrast to this, recognition of a sliding sensation or a surface state is a sensation in a direction along the skin surface of a finger tip of the operator. In addition, this sensation has a directivity within a horizontal plane. In consideration of these points, various methods of satisfying these two conditions and effectively transmitting information have been studied. As a result, it is found that a method of using an elastic plate as a transmit medium and a traveling wave or a standing wave is effective in achieving the above object.

FIG. 13 is a chart showing the displacement states of the mass point of a surface by using a traveling wave and a standing wave, respectively.

The vertex of the traveling wave propagates while drawing an elliptical trace which rotates in a direction opposite to the traveling direction of the traveling wave. The vertex of this elliptic trace is always displaced in the same direction to generate a force in a direction opposite to the traveling direction of the traveling wave. Therefore, an object placed on the vertex of the elliptic trace receives this force to move.

For this reason, when a finger tip is placed on the vertex of the elliptic trace, the finger tip is moved in a reverse direction to the traveling direction of the traveling wave upon propagation of the wave.

At this time, if the finger is intentionally fixed, the traveling wave sequentially propagates on the finger tip. As a result, a sense of sliding of an object on the finger tip can be obtained.

In contrast to this traveling wave, a standing wave generates a force only in the amplitude direction of the wave.

For this reason, when a finger of an operator is placed on the vertex of this wave, the finger receives a vertical force, instead of being moved. As a result, the operator can obtain a sense of touching a sandy object with a rough surface.

Figure 14:
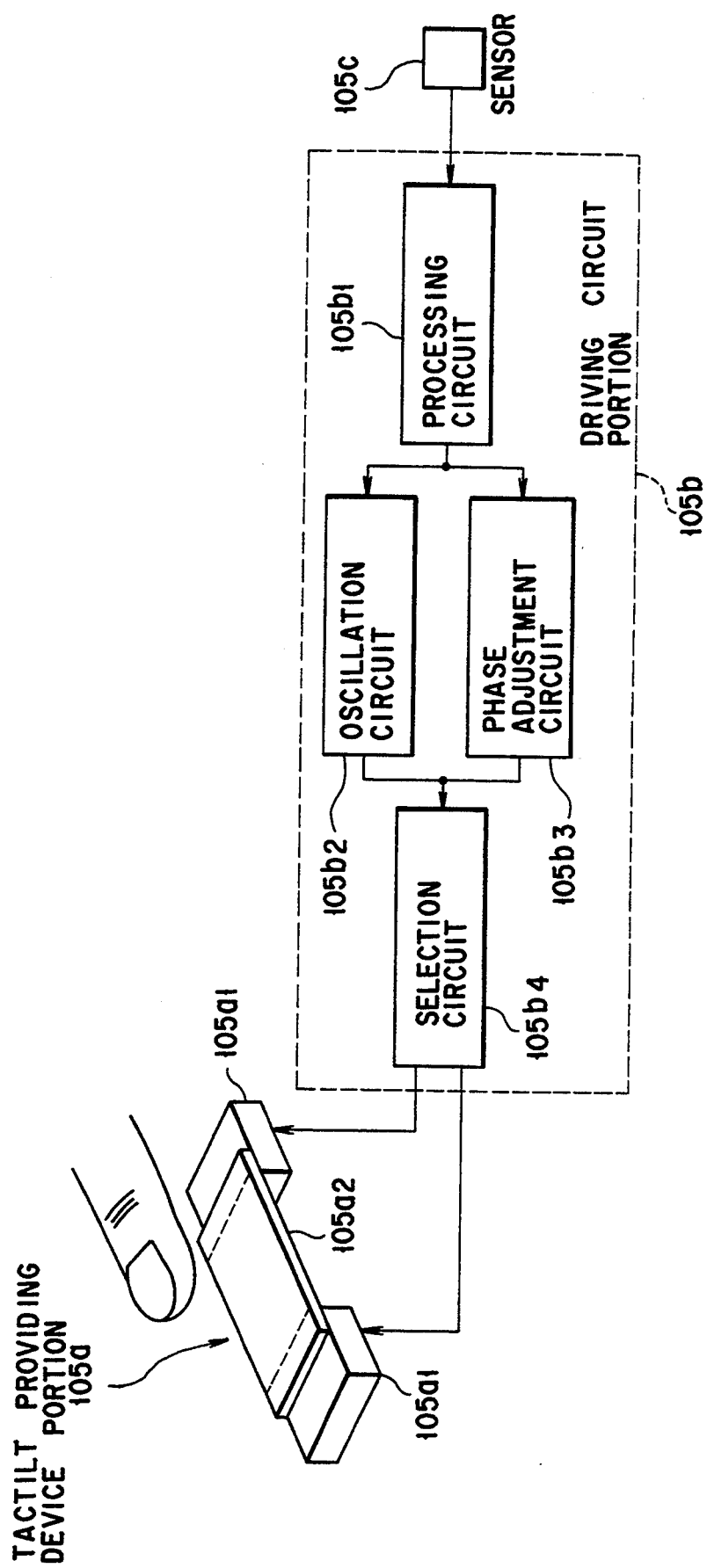
FIG. 14 is a block diagram for explaining the basic arrangement of the tactility providing apparatus according to the second embodiment of the present invention.

In order to solve the above-described problem, a tactility providing apparatus according to the second embodiment of the present invention is constituted by a tactility providing device portion 105a and a driving circuit portion 105b, as shown in FIG. 14.

The tactility providing device portion 105a is constituted by piezoelectric elements 105a1 and a transmission member 105a2 made of an elastic member and designed to transmit vibrations of the piezoelectric elements 105a1. When the piezoelectric elements 105a1 vibrate, a traveling wave is excited on the surface of the transmission member 105a2 to provide a sense of sliding, or a standing wave or a traveling wave including a standing wave is provided to a finger tip of an operator, thus transmitting surface information about an object, such as the surface roughness of the object, to the operator. With this operation, the operator can recognize the texture of the object, improving the operability of the device.

For example, the driving circuit portion 105b includes a processing circuit 105b1 for processing a signal from a sensor 105c and a selection circuit 105b4 coupled to this processing circuit 105b1 via an oscillation circuit 105b2 and a phase adjustment circuit 105b3. The piezoelectric elements 105a1 are driven by outputs from this selection circuit 105b4.

A method of exciting a traveling wave will be described below with reference to an ultrasonic motor as an example.

Figure 15:
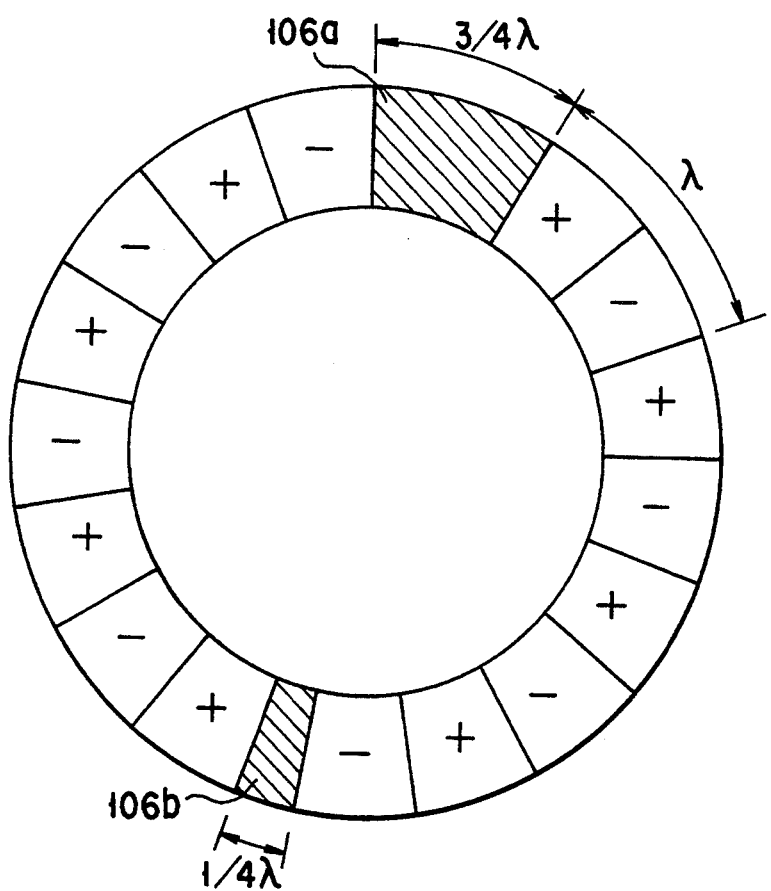
FIG. 15 is a view showing the arrangement of piezoelectric elements constituting a general ultrasonic motor to explain the principle of the tactility providing apparatus according to the second embodiment of the present invention.

FIG. 15 is a chart showing polarized states of piezoelectric elements constituting a general ultrasonic motor.

As shown in FIG. 15, the stator of the ultrasonic motor is generally constituted by a ring-like piezoelectric member alternately polarized in the opposite directions like $+/-/+/-,\ldots$, or a plurality of piezoelectric elements alternately polarized in the opposite directions.

In this arrangement, a pair of adjacent elements polarized in the opposite directions are caused to correspond to one wavelength.

In addition, non-polarized portions 106a and 106b respectively having wavelengths of $\frac{3}{4}\lambda$ and $\frac{1}{4}\lambda$ are arranged at positions separated from each other by 180°, and two sets of $n^2$ polarized portions are arranged to be symmetrical about a central line connecting the non-polarized portions 106a and 106b.

Note that the polarized portions are continuously arranged in the circumferential direction such that the opposite polarization directions alternately appear.

Figure 16:
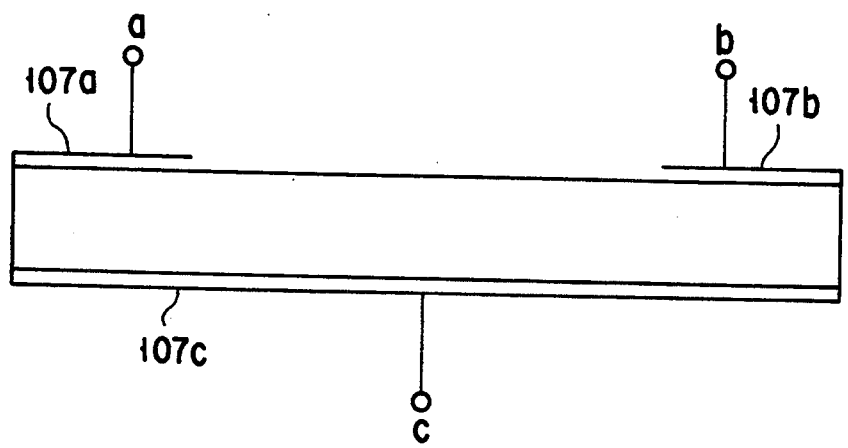
FIG. 16 is a view showing the arrangement of electrodes of the general ultrasonic motor to explain the principle of the tactility providing apparatus of the present invention.

In this polarization arrangement, as shown in FIG. 16, the left half surface, between the $\frac{3}{4}\lambda$ and $\frac{1}{4}\lambda$ non-polarized portions 106a and 106b, which is not in contact with a vibration plate is covered with an electrode as a one-side common electrode 107a, and the right half surface which is not contact in the vibration plate is covered with another electrode as a one-side common electrode 107b.

An electrode 107c of the vibration plate on one side is electrically connected to the vibration plate on the other side to serve as a ground-side electrode common to all the piezoelectric elements.

As shown in FIG. 16, the above structure has three electrical signal input terminals a, b, and c.

When the structure having such polarization and electrode arrangements is to be driven, an electrical signal having a phase difference of $\pi/2$ between the terminals a and c and between the terminals b and c, and a natural frequency ω determined by λ, the inner and outer diameter and thickness of the torus and the average elastic constant and density of the piezoelectric ceramic materials and the vibration plates is input. If a voltage applied between the terminals a and c is represented by:

$$V_0 \sin \omega t$$

then, a voltage applied between the terminals b and c is represented by:

$$V_0 \cos \omega t$$

In general, a displacement y of a given point on a torus based on a traveling wave is represented as follows:

$$y = A \sin(cp - \omega t) \qquad (1)$$

where A is the maximum displacement amount, c is $2c/\lambda$, ω is the natural frequency, and p is the position of the given point on the torus.

According to equation (1), $$y = A \sin 2\pi/\lambda p \cos \omega t + A \sin(2\pi/\lambda p - \pi/2) \sin \omega t \qquad (2)$$

Therefore, a traveling wave can be obtained by superposing waves, represented by the following equations, at a point p:

$$y_1 = A \sin 2\pi/\lambda p \cos \omega t$$

$$y_2 = A \sin 2\pi/\lambda (p - \lambda/4) \sin \omega t$$

The time terms sinωt and cosωt indicate that the vibration has a phase difference π/2 at the point p. In addition, sin2πp/λ and sin2π/λ(p−λ/4) indicate that the position of the wave is shifted by λ/4.

Referring to FIG. 15, the electrode arrangement has the λ/4 and 3λ/4 non-polarized portions for the above-described reason.

As described above, a traveling wave can be obtained by shifting the electrode arrangement by λ/4 and the electrical input signal by π/2.

In such an excited state of a traveling wave, each point on the stator surface draws an elliptic trace at a displacement component $x_p$ in the traveling direction of the traveling wave and a displacement component $y_p$ perpendicular to the surface, as shown in FIG. 17. This phenomenon will be described next.

The vibration of a traveling wave is a wave obtained by a flexural vibration generated by a structure obtained by bonding a piezoelectric ceramic member to a metal plate. Assuming that this flexing uniformly occurs in the direction of thickness of the plate, the displacement component $y_p$ at the surface point p is represented as follows:

$$y_p = A \sin(2\pi/\lambda x_p - \omega t) - e(1 - \cos \theta_p) \qquad (3)$$

where $\theta_p$ is the angle defined by an axis perpendicular to the neutral axis of the torus and the x-axis at the point p, and e is ½ the thickness.

In this case, $\theta_p \neq 0$, and hence equation (3) can be rewritten as:

$$y_p \approx A \sin(2\pi/\lambda x_p - \omega t) \qquad (4)$$

In addition, provided that $\theta_p \approx 0$, the displacement component $x_p$ is:

$$x_p = e \sin \theta_p \approx e \theta_p$$

According to equation (4), $$\theta_p = dy_p/dx_p = AC \cos(2\pi/\lambda x_p - \omega t)$$

$$x_p = ACe \cos(2\pi/\lambda t_p - \omega t) \qquad (5)$$

Consequently, according to equations (4) and (5), $$(\lambda x_p/2Ae\pi)^2 + (y_p/A)^2 = 1 \qquad (6)$$

As is apparent from this, an elliptic trace is drawn.

Since the vertex of this elliptic trace is always displaced in the same direction, an object placed on the vertex of the elliptic trace is moved.

In a general ultrasonic motor, a rotor is placed on the vertex of this elliptic trace to be moved. If a finger tip of an operator is placed on the vertex of the elliptic trace, instead of the rotor, the finger tip is moved in a reverse direction to the propagating direction of the traveling wave upon propagation of the wave. In this case, if the finger tip in intentionally fixed, the traveling wave sequentially propagates on the finger tip. As a result, the operator can obtain a sense of sliding of an object on the finger tip.

Although the above description is associated with a rotary type ultrasonic motor, the same is true for a linear type ultrasonic motor.

In addition, the shape of the motor is not limited to the disk-like shape. Even if a rod- or plate-like motor is used, a traveling wave can be generated on the stator, as long as the same mechanical arrangement as that described above is used.

An ultrasonic motor using a Lengevin oscillator will be described next as another structure for generating a traveling wave.

FIG. 18 shows an example of the ultrasonic motor using a Langevin oscillator. Reference numerals 109a and 109b denote Langevin oscillators. These Langevin oscillators 109a and 109b are oscillated to cause a transmission member 109c to generate a traveling wave, thereby moving a movable member 109d.

A linear type ultrasonic motor can be simply constituted by a device for generating vibrations in such a manner and an elastic member for transmitting a traveling wave generated by the oscillations.

In this motor, an elastic member as a stator has an end portion, unlike the above-described rotary type ultrasonic motor. For this reason, some means must be provided to prevent this end portion from absorbing a traveling wave without reflecting it and interfering with the movement of the traveling wave which is sequentially transmitted.

This problem can be solved by driving the Langevin oscillator on one side such that the oscillation phase matches the traveling wave.

Assume that a traveling wave propagates on the transmission member 109c from the Langevin oscillator 109a to the Langevin oscillator 109b. In this case, when the Langevin oscillator 109b is oscillated with the same phase and period as those of a traveling wave generated by the Langevin oscillator 109a, the traveling wave is absorbed apparently. As a result, the traveling wave from the Langevin oscillator 109a can be continuously transmitted without interfering with propagation of the wave.

In contrast to this, if the phase and period of the oscillation do not match the traveling wave, the traveling wave is reflected by the end portion of the transmission member to interfere with the traveling wave which propagates sequentially, thus locally generating a standing wave. As a result, the traveling wave and the standing wave are mixed together to form a radon waveform. In this case, when a finger tip of an operator is placed on the transmission member, the finger tip is not moved but receives a random displacement instead, thus obtaining a sense of touching a sandy object having a rough surface.

Since a traveling wave and a standing wave can be excited independently or separately, this structure is very effective in providing a sense of sliding and surface roughness.

In addition, with a combination of the above-described second embodiment and the tactility providing apparatus using the electro-mechanical conversion transducers according to the first embodiment, not only surface information about an object but also hardness/softness information as repulsion information associated with deformation of the object can be transmitted to the operator at once.

In the second embodiment described above, when the detection means is brought into contact with an object, a contact state with respect to the object is detected to output a corresponding contact state signal. The contact state signal is then subjected to signal processing in the signal processing means on the basis of the contact state to convert the signal into various types of tactility information such as a sense of sliding of the object, surface roughness, hardness, softness, and the like. When the tactility providing apparatus of the present invention is driven in accordance with the signal, tactility information is transmitted to the operator to allow the operator to sense the contact state with respect to the object and the properties of the object.

Several application examples of the tactility providing apparatus according to the second embodiment of the present invention will be described in detail below with reference to the accompanying drawings.

FIG. 19 shows the first application example based on the second embodiment of the present invention.

Reference numeral 110a denotes a vibration plate as a traveling wave transmission member; and 110b and 110c, piezoelectric elements for generating traveling waves.

In this arrangement, the piezoelectric elements 110b and 110c are respectively used as a piezoelectric element for vibration and a piezoelectric element for absorption. When the piezoelectric elements 110b and 110c are driven to perform phase matching with a wave generated by the piezoelectric element 110b and propagating in the transmission member 110a, a traveling wave is generated on the surface of the transmission member 110a. As a result, the surface of the transmission member 110a is displaced to draw an elliptic trace.

when a finger tip of an operator is placed on the surface of the transmission member 110a at this time, the finger tip is influenced by a tangential force at the wavefront of the elliptic trace to be moved from the piezoelectric element 110b to the piezoelectric element 110c.

In this case, if the finger is fixed, the traveling wave propagates on the finger tip, and only a sense of propagation of the wave is transmitted to the finger tip.

The rotational speed of the elliptic trace can be changed by changing the voltage applied to the piezoelectric element 110b and the driving frequency. By changing the rotational speed of the elliptic trace, the sense of smoothness, received by the finger, can be changed.

If the piezoelectric element 110c is driven with a certain phase so as not to match the phase of a wave propagating in the transmission member 110a, or the driving frequency is shifted, the wave propagating in the transmission member 110a has a waveform like the one obtained by mixing a traveling wave with a standing wave. As a result, the amplitude and direction of the surface displacement become random.

When the finger tip is brought into contact with the transmission member 110a in this state, a random force is transmitted to the finger tip. As a result, the operator obtains a sense of touching a rough surface.

FIG. 20 shows the second application example based on the second embodiment of the present invention.

Reference numeral 111a denotes a vibration plate as a traveling wave transmission member; and 111b and 111c, piezoelectric elements for generating traveling waves.

Although the principle of driving of this application example is the same as that of the first embodiment, a plurality of grooves 111d are formed in the vibration plate 111a in a direction perpendicular to a line connecting the piezoelectric elements 111b and 111c, i.e., a direction perpendicular to the propagating direction of a traveling wave.

With this arrangement, the propagating direction of a traveling wave can be accurately aligned with the line connecting the piezoelectric elements 111b and 111c.

In addition, with the formation of such grooves, a vibration mode of the overall structure can be optimized, and generation of unnecessary mode components can be prevented. Therefore, a traveling wave is allowed to efficiently propagate.

For this reason, according to this application example, a clear sense of sliding, surface information, or the like can be transmitted.

Figure 21:
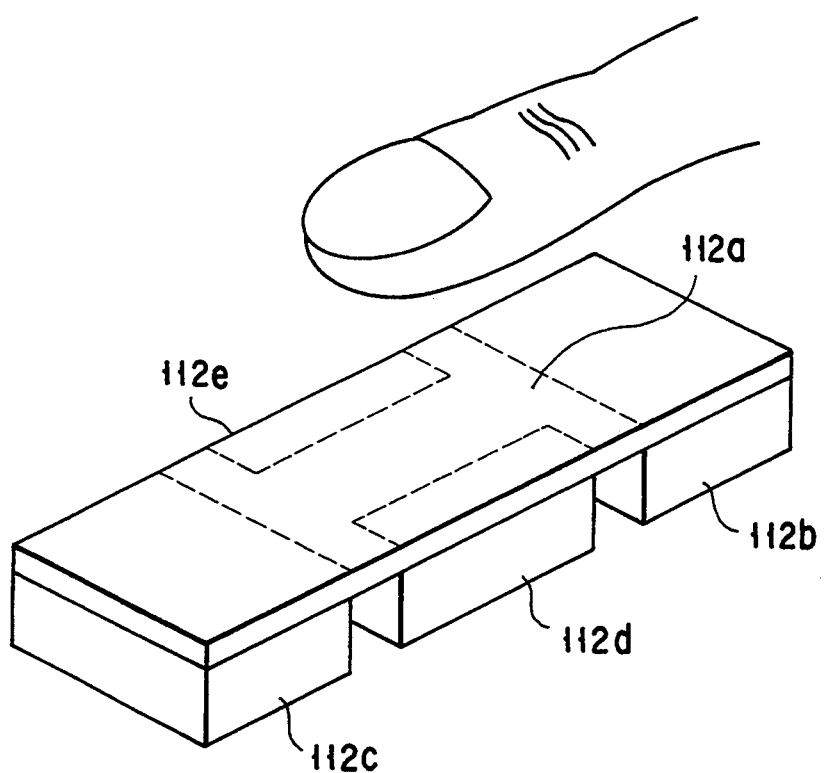
FIG. 21 is a perspective view showing the third application example based on the second embodiment of the present invention.

FIG. 21 shows the third application example based on the second embodiment of the present invention.

Reference numeral 112a denotes a vibration member as a traveling wave transmission member; and 112b, 112c, 112d, and 112e, piezoelectric elements for generating traveling waves.

The piezoelectric elements 112d and 112e are arranged at right angles with respect to the piezoelectric elements 112b and 112c.

In this arrangement, the piezoelectric elements 112b and 112d are used for vibration, and the piezoelectric elements 112c and 112e are used for absorption. By transmitting traveling waves with the piezoelectric elements 112b and 112c serving as a pair, and the piezoelectric elements 112d and 112e serving as another pair, two types of traveling waves having an angle difference of 90° are allowed to propagate on the transmission member 112a.

With this arrangement, the operator can sense whether the sense of sliding, described in the first application example, acts in a direction perpendicular or parallel to the fingertip.

Figure 22:
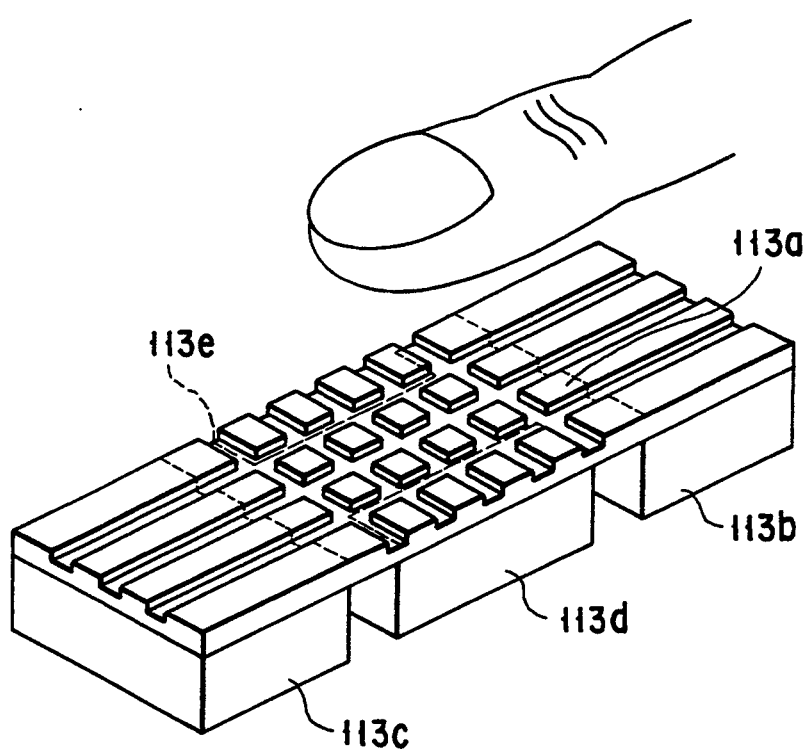
FIG. 22 is a perspective view showing the fourth application example based on the second embodiment of the present invention.

FIG. 22 shows the fourth application example based on the second embodiment of the present invention.

Reference numeral 113a denotes a vibration plate as a traveling wave transmission member; and 113b, 113c, 113d, and 113e, piezoelectric elements for generating traveling waves.

Although the principle of driving of this application example is the same as that of the third application example, grooves are formed in the vibration plate 113a in directions along a line connecting the piezoelectric elements 113b and 113c and a line connecting the piezoelectric elements 113d and 113e, i.e., directions perpendicular to the propagating directions of traveling waves.

With this arrangement, the propagating directions of traveling waves can be accurately aligned with the line connecting the piezoelectric elements 113b and 113c and the line connecting the piezoelectric elements 113d and 113e.

In addition, with the formation of such grooves, a vibration mode of a overall structure can be optimized, and generation of unnecessary mode components can be prevented. Therefore, traveling waves are allowed to efficiently propagate.

For this reason, according to this application example, a clear sense of sliding, surface information, or the like can be transmitted.

FIG. 23 shows the fifth application example based on the second embodiment of the present invention, which is obtained by extending the fourth embodiment.

Reference numeral 114a denotes a vibration plate as a traveling wave transmission member; and 114b, 114c, 114d, 114e, 114f, 114g, 114h, and 114i, piezoelectric elements.

Grooves 114j are formed in the vibration plate 114a in advance to accurately propagate traveling waves.

The piezoelectric elements 114b, 114c, 114d, 114e, 114f, 114g, 114h, and 114i are spaced apart from each other to prevent vibrations generated by the respective elements from being influenced by each adjacent piezoelectric element.

In this arrangement, the piezoelectric elements 114b and 114f, 114c and 114g, 114d and 114h, and 114e and 114i are paired, respectively, and the elements of each pair respectively serve as a piezoelectric element for vibration and a piezoelectric element for absorption so as to propagate a traveling wave.

In this arrangement, since the respective pairs are shifted from each other by 45°, senses of sliding in four directions can be obtained. In addition, by reversing the vibration phases of the piezoelectric elements of each pair to exchange the roles of the piezoelectric elements as a vibration element and an absorption element, senses of sliding in a total of eight directions can be obtained.

Note that this reversal of vibration phases can be applied to all the application examples based on the second embodiment of the present invention.

In this application example, four pairs of vibration and absorption elements are constituted by a total of eight piezoelectric elements. If, however, the number of piezoelectric elements is increased to increase the number of pairs of vibration and absorption elements, senses of sliding in a larger number of directions can be obtained.

FIG. 24 shows the sixth application example based on the second embodiment of the present invention, to which the fifth application example is applied.

Reference numeral 115a denotes a vibration plate as a traveling wave transmission member; and 115b, a piezoelectric element.

Figure 25:
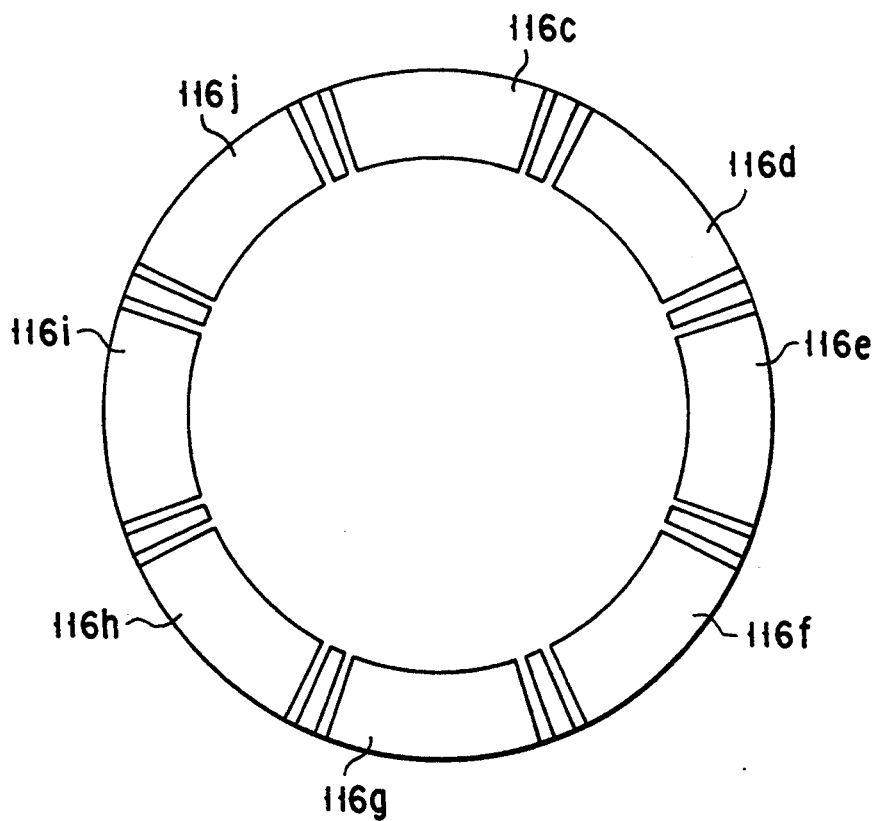
FIG. 25 is a plan view showing the arrangement of piezoelectric elements used in the sixth application example based on the second embodiment of the present invention.

The piezoelectric element 115b is arranged in the manner shown in FIG. 25. Reference numerals 116c, 116d, 116e, 116f, 116g, 116h, 116i, and 116j denote piezoelectric elements for generating traveling waves.

The piezoelectric elements 116c, 116d, 116e, 116f, 116g, 116h, 116i, and 116j and elastic members joining them together are spaced apart from each other to prevent vibrations, generated by these elements, from being influenced by each adjacent piezoelectric element.

In this arrangement, the piezoelectric elements 116c and 116g, 116d and 116h, 116e and 116i, and 116f and 116j are paired, respectively, and these pairs generate traveling waves.

As in this application example, even if a transmission member is formed into a circular shape, and piezoelectric elements are arranged in an arcuated form in accordance with this circular shape, the function described with reference to the fifth application example can be satisfied.

In this example, senses of sliding in a total of eight directions can be obtained. If, however, the number of piezoelectric elements is increased to increase the number of pairs of vibration and absorption elements, senses of sliding in a larger number of directions can be obtained.

Figure 26:
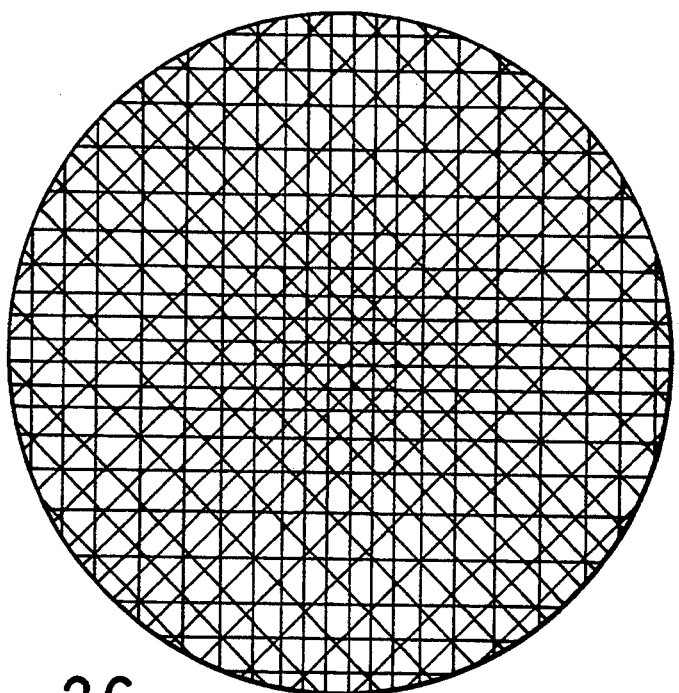
FIG. 26 is a plan view showing the seventh application example based on the second embodiment of the present invention.
Figure 34A:
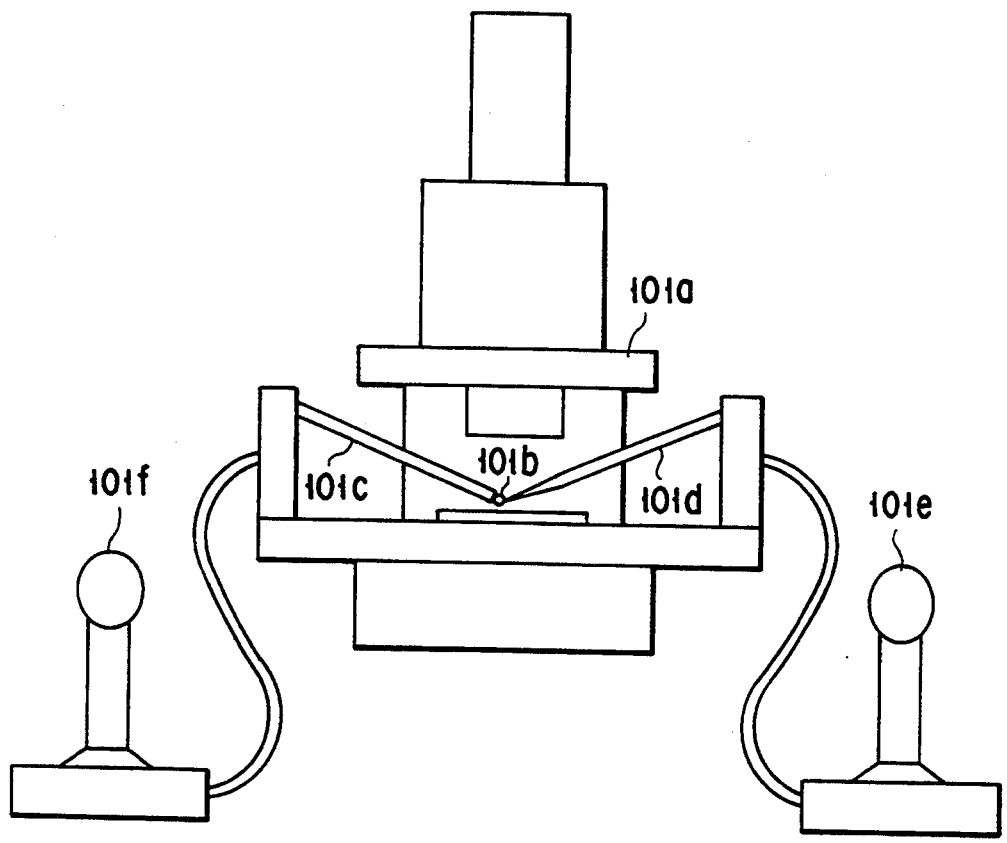
FIGS. 34A and 34B are views showing a prior art associated with a microscope.
Figure 34B:
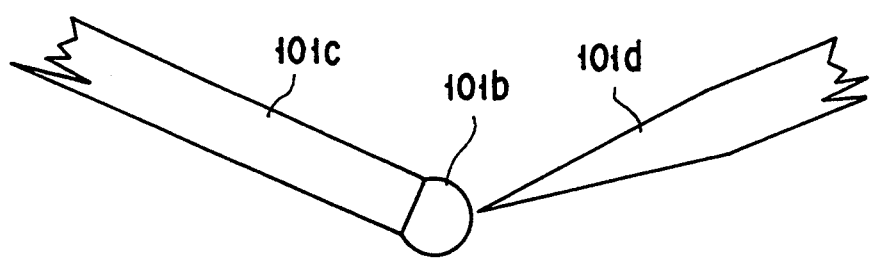
Figure 35:
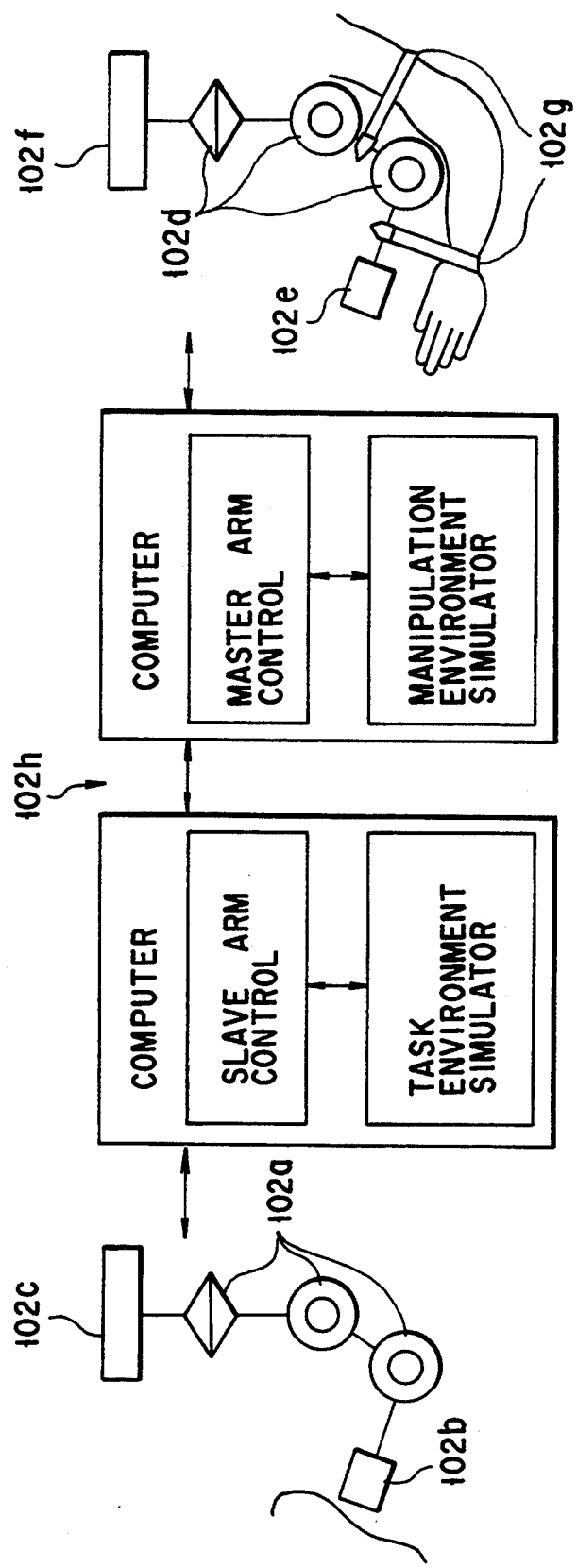
FIG. 35 is a view showing a prior art associated with a robot manipulator.
Figure 36A:
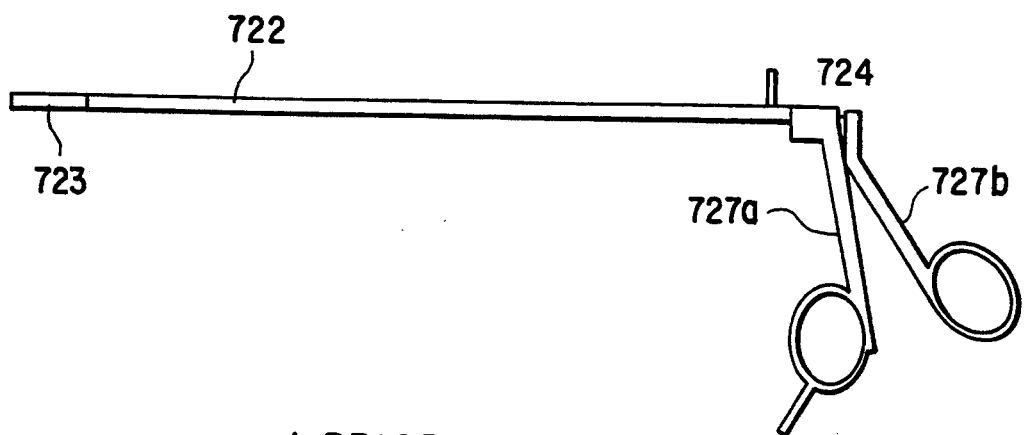
FIGS. 36A and 36B are views showing a prior art associated with a forceps.
Figure 36B:
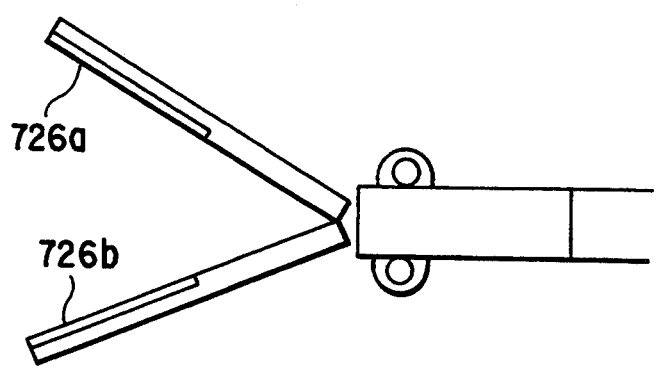

FIG. 26 shows the seventh application example based on the second embodiment of the present invention, in which grooves are formed in the vibration plate 115a as the traveling wave transmission member, described in the sixth embodiment, in directions perpendicular to the propagating directions of traveling waves generated by the respective pairs of piezoelectric elements.

With this arrangement, a vibration mode of the overall structure can be optimized, and generation of unnecessary mode components can be prevented. As a result, traveling waves are allowed to efficiently propagate. Therefore, clear senses of sliding, surface information, or the like can be transmitted.

The grooves described in the seventh application example effectively work even if they are formed concentrically as in the eight application example based on the second embodiment of the present invention, which is shown in FIG. 27.

FIG. 28 shows the ninth application example based on the second embodiment of the present invention.

Reference numeral 119a denotes a vibration plate as a traveling wave transmission member; and 119b and 119c, piezoelectric elements for generating traveling waves.

A plurality of plate-like members 119d are fixed on the vibration plate 119a.

The members 119d serve to amplify the amplitudes of traveling waves excited by the piezoelectric elements 119b and 119c, thus forming clearer traveling waves.

In addition, the members 119d also serve to optimize a vibration mode as in the second, fourth, seventh, and eighth application examples. With this function, generation of unnecessary mode components can be prevented. Therefore, a clear sense of sliding, surface information, or the like can be transmitted.

FIG. 29 shows the tenth application example based on the second embodiment of the present invention.

Reference numeral 120a denotes a vibration plate as a traveling wave transmission member; and 120b and 120c, piezoelectric for generating traveling waves.

The tenth embodiment is effective in transmitting a clear sense of sliding, surface information, or the like by optimizing a vibration mode as in the second, fourth, seventh, eight, and ninth application examples. In addition, since the tenth application example has the same function as that of the second, fourth, seventh, eighth, or ninth example, the tenth application example is effective in a case wherein grooves cannot be formed in a transmission member surface.

FIG. 30 shows the eleventh application example based on the second embodiment of the present invention.

Reference numeral 121a denotes a vibration plate as a traveling wave transmission member; 121b and 121c, piezoelectric elements for generating traveling waves; and 121d and 121e, ultrasonic shielding members.

As is apparent from the description of each application example based on the second embodiment of the present invention, in the method of exciting traveling waves or standing waves on an elastic member as a transmission medium by driving piezoelectric elements, it is important to provide some means to efficiently transmit vibrations of the piezoelectric elements to the transmission medium.

This application example shows a technique of achieving this object. In the application example, the piezoelectric elements 121b and 121c are mounted on the ultrasonic shielding members 121d and 121e in such a manner that the contact points between the piezoelectric elements 121b and 121c and the ultrasonic shielding members 121d and 121e coincide with nodes of vibrations of the piezoelectric elements 121b and 121c.

With this arrangement, since no displacement occurs at the contact points when vibrations are generated by the piezoelectric elements 121b and 121c, the vibrations do not propagate to the ultrasonic shielding members 121d and 121e, preventing attenuation of the vibrations owing to the contact. Therefore, the vibrations of the piezoelectric elements 121b and 121c can be efficiently transmitted to the transmission member 121a to excite traveling waves or standing waves.

FIG. 31 shows the twelfth application example based on the second embodiment of the present invention.

Reference numeral 122a denotes a vibration plate as a traveling wave transmission member; 122b and 122c, piezoelectric elements for generating traveling waves; and 122d, an ultrasonic shielding member.

The technique of efficiently transmitting vibrations of piezoelectric elements to a transmission member as in the eleventh application example can also be realized by the arrangement of the twelfth application example shown in FIG. 31. In this application example, the ultrasonic shielding member 122d has a low ultrasonic transmission efficiency.

If the piezoelectric elements 122b and 122c are mounted on the ultrasonic shielding member 122d, vibrations of the piezoelectric elements 122b and 122c can be efficiently transmitted to the transmission member 122a to excite traveling waves or standing waves.

FIG. 32 shows the thirteenth application example based on the second embodiment of the present invention.

Reference numeral 123a denotes a vibration plate as a traveling wave transmission member; 123b and 123c, piezoelectric elements for generating traveling waves; 123d, a coil; 123e and 123f, permanent magnets; 123g, a shaft; 123h, a base; 123i, a board; and 123j, an ultrasonic shielding member.

The piezoelectric elements 123b and 123c are arranged on the board 123i via the ultrasonic shielding member 123j so that vibrations of the piezoelectric elements 123b and 123c can be efficiently transmitted to the vibration plate 123a.

In this arrangement, the voice coil constituted by the coil 123d and the permanent magnets 123e and 123f as in the first embodiment is combined with the tactility providing apparatus as in the first to twelfth application examples based on the second embodiment.

The transmission member 123a constitutes a voice coil together with the magnetic circuit formed therebelow. The transmission member 123a can be vibrated vertically or can be caused to protrude by a current supplied to this system.

The tactility transmission function of this voice coil is the same as that disclosed in the first embodiment of the present invention. That is, the transmission member 123a is driven at a frequency corresponding to the time response limit associated with human tactility to allow an operator to sense the hardness/softness of an object. In addition, a repulsion generated when the object is pressed can be expressed by a force of a current, with which the transmission member 123a is held.

By using the arrangement of this application example, a sense of hardness/softness of an object, surface information, and a sense of sliding can be transmitted to the operator.

FIG. 33 shows the fourteenth application example based on the second embodiment of the present invention.

FIG. 33 is a block diagram schematically showing a typical circuit arrangement of the thirteenth application example in FIG. 32, which is based on the second embodiment of the present invention.

This circuit arrangement is constituted by a sensor circuit 124b, a sense signal conversion circuit 124c, a sense signal-oscillation frequency value conversion circuit 124d, a sense signal-phase value conversion circuit 124e, an oscillation circuit 124f, a phase adjustment circuit 124g, a selection circuit 124h, and a driving circuit 124k. The circuit arrangement is designed to drive piezoelectric elements 124i and 124j and a voice coil 124l.

Consider a signal transmission path. A signal from a sensor 124a is input to the sensor circuit 124b for processing a sensor output. The signal is then input to the sense signal conversion circuit 124c for converting the output from the sensor circuit 124b into a sense signal representing hardness/softness, a sense of sliding, or the like, and also performing branch processing.

Thereafter, the sense signal representing hardness/softness is transmitted to the driving circuit 124k for the voice coil. The voice coil 24l is driven on the basis of the driving signal processed by the driving circuit 124k.

Meanwhile, the sense signal representing a sense of sliding and surface roughness is processed by the sense signal-oscillation frequency value conversion circuit 124d and the sense signal-phase value conversion circuit 124e. The resultant oscillation frequency value and phase value are sent to the oscillation circuit 124f and the phase adjustment circuit 124g.

In addition, phase information based on the sense signal, i.e., information for controlling the amplitude and direction of a surface displacement, is input to the sense signal-phase value conversion circuit 124e. Thereafter, the information is sent to the phase adjustment circuit 124g for adjusting a driving phase for exciting a traveling wave or a standing wave.

As described in the sixth application example, the respective signals are input to the selection circuit 124h for selecting a specific pair of piezoelectric element elements from a plurality of piezoelectric element elements. The signals then drive the piezoelectric elements 124$i$ and 124$j$ to provide a traveling wave or a standing wave to the vibration plate as the transmission member.

As has been described above, according to the second embodiment of the present invention, tactility information is transmitted to an operator so as to allow the operator to obtain a sense of actually manipulating an object with his/her hand. Therefore, in the use of a conventional device like the one described in "Description of the Related Art", a sense of detachment with respect to an operation can be eliminated to improve the operability of the device, thereby allowing a more accurate operation with higher operability.

Additional embodiments of the present invention will be apparent to those skilled in the art from consideration of the specification and practice of the present invention disclosed herein. It is intended that the specification and examples be considered as exemplary only, with the true scope of the present invention being indicated by the following claims.

What is claimed is:

1. A tactility providing apparatus comprising:
   detection means for outputting a contact state signal in accordance with a contact state with respect to an object to be manipulated, the contact state signal representing at least one of information of a sense of sliding of said detection means with respect to the object and surface information such as surface roughness of the object;
   signal processing means for converting the contact state signal from said detection means into tactility information corresponding to at least one of the information of the sense of sliding and the surface information;
   tactility providing means which is excited in accordance with the tactility information from said signal processing means to generate at least one of a traveling wave corresponding to the information of the sense of sliding and a standing wave corresponding to the surface information; and
   transmission means for transmitting at least one of the traveling wave and the standing wave generated by said tactility providing means to a finger of an operator,
   wherein while the finger of the operator is in a non-contact state with respect to the object, the information of the sense of sliding with respect to the object is provided to the finger, through the traveling wave transmitted from said transmission means, in accordance with the contact state signal from said detection means, and the surface information about the object is also provided to the finger through the standing wave.

2. An apparatus according to claim 1, wherein said tactility providing means includes a proper number of piezoelectric elements.

3. An apparatus according to claim 2, wherein said piezoelectric elements include first and second piezoelectric elements arranged to oppose each other at a predetermined distance, and said transmission means includes a vibration member arranged between said first and second piezoelectric elements.

4. An apparatus according to claim 3, wherein said first piezoelectric element is used for oscillation, and said second piezoelectric element is used for absorbing a vibration.

5. An apparatus according to claim 4, wherein a proper number of grooves are formed in said vibration member to be perpendicular to a propagating direction of a traveling wave propagating in said vibration member.

6. An apparatus according to claim 4, wherein third and fourth piezoelectric elements are attached to an intermediate portion of said vibration member to be perpendicular to a propagating direction of a traveling wave propagating in said vibration member.

7. An apparatus according to claim 6, wherein a proper number of grooves are formed in said vibration member in a direction perpendicular to a propagating direction of a traveling wave propagating in said vibration member.

8. An apparatus according to claim 2, wherein said piezoelectric elements include first to eighth piezoelectric elements arranged at angular intervals of 45° to oppose each other at a predetermined interval, and said transmission means is arranged between said first to eighth piezoelectric elements and includes a vibration member having a substantially octagonal outer shape and a proper number of grooves formed in correspondence with directions in which said first to eight piezoelectric elements oppose each other.

9. An apparatus according to claim 2, wherein said piezoelectric elements include first to eighth arcuated piezoelectric elements respectively arranged at positions determined by dividing a circumference into eight equal parts, and said transmission means includes a circular vibration member arranged on said first to eighth arcuated piezoelectric elements.

10. An apparatus according to claim 9, wherein a proper number of grooves are formed in said circular vibration member to be perpendicular to propagating directions of traveling waves propagating between said first to eighth arcuated piezoelectric elements.

11. An apparatus according to claim 9, wherein said circular vibration member has a proper number of concentrical grooves.

12. An apparatus according to claim 4, wherein a proper number of plate-like members are formed upright on said vibration member to be perpendicular to a propagating direction of a traveling wave propagating in said vibration member.

13. An apparatus according to claim 5, wherein said proper number of grooves are formed in a lower surface of said vibration member.

14. An apparatus according to claim 4, wherein said first and second piezoelectric elements are mounted on first and second ultrasonic shielding members, respectively.

15. An apparatus according to claim 4, wherein said first and second piezoelectric elements are mounted on a common ultrasonic shielding member.

16. A tactility providing apparatus comprising:
   detection means for outputting a contact state signal in accordance with a contact state with respect to an object to be manipulated, the contact state signal representing at least one of information of a sense of sliding of said detection means with respect to the object and surface information such as surface roughness of the object, and hardness information such as hardness/softness of the object;
   signal processing means for converting the contact state signal from said detection means into first tactility information corresponding to at least one of the information of the sense of sliding and the surface information, and also converting the contact state signal into second tactility information corresponding to the hardness information;

first tactility providing means which is excited in accordance with the first tactility information from said signal processing means to generate at least one of a traveling wave corresponding to the information of the sense of sliding and a standing wave corresponding to the surface information;

second tactility providing means which is excited in accordance with the second tactility information from said signal processing means to generate a pressure corresponding to the hardness information; and transmission means for transmitting at least one of the traveling wave and the standing wave generated by said first tactility providing means to a finger of an operator together with the pressure generated by said second tactility providing means, wherein while the finger of the operator is in a non-contact state with respect to the object, the information of the sense of sliding with respect to the object is provided to the finger, through the traveling wave transmitted from said transmission means, in accordance with the contact state signal from said detection means, the surface information about the object is provided to the finger through the standing wave, and the hardness information about the object is also provided to the finger through the pressure.

17. An apparatus according to claim 16, wherein said first tactility providing means includes an oscillation piezoelectric element and an absorption piezoelectric element arranged to oppose each other at a predetermined distance, said transmission means includes a vibration member arranged between said oscillation piezoelectric element and said absorption piezoelectric element, and said second tactility providing means includes a voice coil constituted by a coil coupled to said vibration member via said oscillation piezoelectric element and said absorption piezoelectric element, and a magnetic circuit magnetically coupled to said coil.

18. An apparatus according to claim 17, wherein said voice coil is coupled to said vibration member via an ultrasonic shielding member on which said oscillation piezoelectric element and said absorption piezoelectric element are mounted.

19. An apparatus according to claim 1, further comprising:

an operating portion, having said detection means, for bringing said detection means into contact with said object and for carrying out a predetermined work on said object;

a manipulation portion, having said transmission means, for transmitting tactility information to an operator by said transmission means, said manipulation portion being manipulated by the operator so that said operating portion carries out a predetermined operation; and a control section, having said signal processing means for converting/outputting tactility information about the object on the basis of the contact state signal based on the object and output from said detection means of said operating means, for controlling said transmission means in accordance with the processed signal and controlling movement of said operating portion in accordance with movement of said manipulating portion.

20. An apparatus according to claim 1, wherein said signal processing means converts tactility information of the object into a frequency exceeding a time response limit of tactility of a human being on the basis of the contact state detected by said detection means, and outputs the frequency.

* * * * *